United States Patent
Blanchard

(10) Patent No.: US 12,359,159 B2
(45) Date of Patent: *Jul. 15, 2025

(54) CELL CULTURE INCUBATORS WITH INTEGRATED CELL MANIPULATION SYSTEMS

(71) Applicant: Thrive Bioscience, Inc., Beverly, MA (US)

(72) Inventor: Alan Blanchard, Topsfield, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,569

(22) Filed: Feb. 1, 2024

(65) Prior Publication Data

US 2024/0309308 A1 Sep. 19, 2024

Related U.S. Application Data

(63) Continuation of application No. 17/718,570, filed on Apr. 12, 2022, now Pat. No. 11,920,122, which is a
(Continued)

(51) Int. Cl.
*C12M 1/00* (2006.01)
*C12M 1/34* (2006.01)
(Continued)

(52) U.S. Cl.
CPC ............ *C12M 41/14* (2013.01); *C12M 41/36* (2013.01); *C12M 41/40* (2013.01); *C12M 41/48* (2013.01);
(Continued)

(58) Field of Classification Search
CPC ...... C12M 41/14; C12M 41/40; C12M 41/48; C12M 41/36; G01N 15/1463;
(Continued)

(56) References Cited

U.S. PATENT DOCUMENTS 3,887,436 A 6/1975 Haddad et al.
4,871,676 A 10/1989 Yamada
(Continued)

FOREIGN PATENT DOCUMENTS

CN 101313196 A 11/2008
CN 101501180 A 8/2009
(Continued)

OTHER PUBLICATIONS

Machine Translation of CN 102459560 A (Year: 2025).*
(Continued)

*Primary Examiner* — Michael L Hobbs
(74) *Attorney, Agent, or Firm* — Wolf, Greenfield & Sacks, P.C.

(57) ABSTRACT

A cell culture incubator has an incubator cabinet with an internal chamber for the incubation of cells in one or more cell culture vessels and a door opening from an external environment to the internal chamber. At least two imagers configured for imaging the cells are within the internal chamber and a manipulator for manipulating the cells in the one or more cell culture vessels is within the internal chamber. A cell culture vessel transfer device moves the one or more cell culture vessels between the at least two imagers within the internal chamber and a controller is configured for controlling the cell culture transfer device to move cell culture vessels between the at least two imagers.

13 Claims, 17 Drawing Sheets

Related U.S. Application Data continuation of application No. 15/931,927, filed on May 14, 2020, now Pat. No. 11,332,705, which is a continuation of application No. 15/563,383, filed as application No. PCT/US2016/025356 on Mar. 31, 2016, now Pat. No. 10,696,937.

(60) Provisional application No. 62/141,191, filed on Mar. 31, 2015.

(51) Int. Cl.
  *C12M 1/36* (2006.01)
  *G01N 15/1433* (2024.01)
  *G01N 35/00* (2006.01)
  *G01N 15/10* (2006.01)
  *G01N 15/1434* (2024.01)
  *G01N 35/04* (2006.01)

(52) U.S. Cl.
  CPC ... *G01N 15/1433* (2024.01); *G01N 35/00732* (2013.01); *G01N 35/0099* (2013.01); *G01N 2015/1006* (2013.01); *G01N 2015/1454* (2013.01); *G01N 2035/00356* (2013.01); *G01N 2035/0463* (2013.01)

(58) Field of Classification Search
  CPC ......... G01N 35/00732; G01N 35/0099; G01N 2015/1006; G01N 2015/1454; G01N 2035/00356; G01N 2035/0463
  See application file for complete search history.

(56) References Cited

U.S. PATENT DOCUMENTS

| | | | |
|---|---|---|---|
| 5,906,943 A | 5/1999 | Skropik et al. | |
| 5,958,763 A | 9/1999 | Goffe | |
| 6,465,244 B1 | 10/2002 | Annable et al. | |
| 7,540,844 B2 | 6/2009 | Muser | |
| 8,548,745 B2 | 10/2013 | Callahan et al. | |
| 9,857,360 B2 | 1/2018 | Lim | |
| 10,201,896 B2 | 2/2019 | Kihara et al. | |
| 10,696,937 B2 | 6/2020 | Blanchard | |
| 10,969,937 B2 * | 4/2021 | Schwarz ............... G06F 3/011 | |
| 11,034,927 B2 | 6/2021 | Blanchard | |
| 11,168,297 B2 | 11/2021 | Blanchard | |
| 11,319,523 B2 | 5/2022 | Blanchard | |
| 11,332,705 B2 | 5/2022 | Blanchard | |
| 11,879,120 B2 | 1/2024 | Blanchard | |
| 11,920,121 B2 | 3/2024 | Blanchard | |
| 11,920,122 B2 * | 3/2024 | Blanchard ........ G01N 35/00732 | |
| 12,098,358 B2 | 9/2024 | Blanchard | |
| 12,180,454 B2 | 12/2024 | Blanchard | |
| 2001/0039032 A1 | 11/2001 | Matsumura et al. | |
| 2002/0090320 A1 | 7/2002 | Burrow et al. | |
| 2002/0146347 A1 | 10/2002 | McNeil et al. | |
| 2003/0040104 A1 | 2/2003 | Barbera-Guillem | |
| 2004/0029266 A1 | 2/2004 | Barbera-Guillem | |
| 2004/0064013 A1 | 4/2004 | Attias | |
| 2004/0215362 A1 | 10/2004 | Kokubo | |
| 2005/0170491 A1 | 8/2005 | Takagi | |
| 2005/0239040 A1 | 10/2005 | Lindenberg | |
| 2005/0260743 A1 * | 11/2005 | Drake ................... C12M 41/48 | |
| | | | 702/19 |
| 2006/0177922 A1 | 8/2006 | Shamah et al. | |
| 2006/0194193 A1 | 8/2006 | Tsuruta et al. | |
| 2006/0275888 A1 | 12/2006 | Hibino et al. | |
| 2008/0090288 A1 | 4/2008 | Hibino et al. | |
| 2010/0099177 A1 | 4/2010 | Yang et al. | |
| 2010/0291619 A1 | 11/2010 | Robinson et al. | |
| 2010/0330651 A1 | 12/2010 | Venter et al. | |
| 2011/0027146 A1 | 2/2011 | Yokoi et al. | |
| 2012/0092478 A1 | 4/2012 | Honda et al. | |
| 2012/0122138 A1 | 5/2012 | Randles et al. | |
| 2012/0122143 A1 | 5/2012 | Mimura et al. | |
| 2012/0164721 A1 | 6/2012 | Kobayashi et al. | |
| 2012/0196316 A1 | 8/2012 | Sebesta et al. | |
| 2013/0074614 A1 | 3/2013 | Holmes et al. | |
| 2013/0079236 A1 | 3/2013 | Holmes | |
| 2013/0130361 A1 | 5/2013 | Okano et al. | |
| 2013/0162795 A1 | 6/2013 | Wong et al. | |
| 2013/0210130 A1 | 8/2013 | Larcher et al. | |
| 2013/0273646 A1 | 10/2013 | Kobayashi et al. | |
| 2013/0316442 A1 | 11/2013 | Meurville et al. | |
| 2014/0051156 A1 | 2/2014 | Miyake et al. | |
| 2014/0057342 A1 | 2/2014 | Uozumi et al. | |
| 2014/0106386 A1 | 4/2014 | Umeno et al. | |
| 2014/0106389 A1 | 4/2014 | Loewke et al. | |
| 2014/0273191 A1 | 9/2014 | Tipgunlakant et al. | |
| 2015/0037206 A1 | 2/2015 | Akutsu | |
| 2015/0079584 A1 | 3/2015 | Gevaert et al. | |
| 2015/0079621 A1 | 3/2015 | An et al. | |
| 2015/0278625 A1 | 10/2015 | Finkbeiner et al. | |
| 2015/0298123 A1 | 10/2015 | Block, III et al. | |
| 2015/0322479 A1 | 11/2015 | Pettigrew et al. | |
| 2017/0137770 A1 | 5/2017 | Sakamoto et al. | |
| 2017/0361468 A1 | 12/2017 | Cheuvront et al. | |
| 2018/0066218 A1 | 3/2018 | Koike et al. | |
| 2018/0079999 A1 | 3/2018 | Blanchard | |
| 2018/0087020 A1 | 3/2018 | Blanchard | |
| 2018/0087021 A1 | 3/2018 | Blanchard | |
| 2018/0346868 A1 | 12/2018 | Blanchard | |
| 2020/0102528 A1 | 4/2020 | Horcajadas Almansa et al. | |
| 2020/0347339 A1 | 11/2020 | Blanchard | |
| 2020/0348324 A1 | 11/2020 | Wikholm et al. | |
| 2021/0222110 A1 | 7/2021 | Blanchard | |
| 2021/0261903 A1 | 8/2021 | Blanchard | |
| 2022/0243167 A1 | 8/2022 | Blanchard | |
| 2022/0259546 A1 | 8/2022 | Blanchard | |
| 2023/0303959 A1 | 9/2023 | Blanchard | |
| 2024/0228936 A1 | 7/2024 | Blanchard | |
| 2024/0294861 A1 | 9/2024 | Blanchard | |
| 2024/0409871 A1 | 12/2024 | Blanchard | |

FOREIGN PATENT DOCUMENTS

| | | | | |
|---|---|---|---|---|
| CN | 101987205 A | | 3/2011 | |
| CN | 102174395 A | | 9/2011 | |
| CN | 102321522 A | | 1/2012 | |
| CN | 102459560 A | * | 5/2012 | ............ C12M 23/14 |
| CN | 102471744 A | | 5/2012 | |
| CN | 104245917 A | | 12/2014 | |
| EP | 1 460 126 A2 | | 9/2004 | |
| EP | 1 471 138 A1 | | 10/2004 | |
| EP | 1 553 166 A1 | | 7/2005 | |
| EP | 1 598 415 A1 | | 11/2005 | |
| EP | 1 650 291 A1 | | 4/2006 | |
| JP | 58-036383 | | 3/1983 | |
| JP | H02-171866 A | | 7/1990 | |
| JP | 2003-052365 A | | 2/2003 | |
| JP | 2003-174870 A | | 6/2003 | |
| JP | 2004-511788 A | | 4/2004 | |
| JP | 2004-321111 A | | 11/2004 | |
| JP | 2005-102570 A | | 4/2005 | |
| JP | 2006-101781 A | | 4/2006 | |
| JP | 2006-174828 A | | 7/2006 | |
| JP | 2006-284288 A | | 10/2006 | |
| JP | 2009-511998 A | | 3/2009 | |
| JP | 3157029 U | | 1/2010 | |
| JP | 210-154792 A | | 7/2010 | |
| JP | 2010-273603 A | | 12/2010 | |
| JP | 2011-030655 A | | 2/2011 | |
| JP | 2012-130297 A | | 7/2012 | |
| JP | 2012-524268 A | | 10/2012 | |
| JP | 2013-009618 A | | 1/2013 | |
| JP | 2018510660 A | * | 4/2018 | ............ C12M 23/16 |
| WO | WO 98/24883 A2 | | 6/1998 | |
| WO | WO 2005/009126 A1 | | 2/2005 | |
| WO | WO 2011/010449 A1 | | 1/2011 | |
| WO | WO 2011/089908 A1 | | 7/2011 | |
| WO | WO 2011/091333 A1 | | 7/2011 | |
| WO | WO 2013/016248 A1 | | 1/2013 | |

(56) References Cited

FOREIGN PATENT DOCUMENTS

| WO | WO 2014/044823 A1 | 3/2014 |
|----|-------------------|--------|
| WO | WO 2012/098931 A1 | 6/2014 |
| WO | WO 2015/019595 A1 | 2/2015 |

OTHER PUBLICATIONS

Machine Translation of JP 2018510660 A (Year: 2025).*
Extended European Search Report in connection with Application No. EP 16774240.2 mailed on Mar. 29, 2019.
International Search Report and Written Opinion for Application No. PCT/US2016/025356 mailed Sep. 15, 2016.
International Preliminary Report on Patentability for Application No. PCT/US2016/025356 mailed Oct. 12, 2017.
[No Author Listed] Incubator Fluorescence Microscope LCV110U Viva View FL. 2008. Brochure by Olympus America. Retrieved from the Internet <http://www.olympus-lifesience.com/en/microscopes/inverted/incubator/#!cms[tab]=%2Fmicroscopes%2Finverted%2Fincubator%2Fresources>.; p. 5.
[No Author Listed], Digital holographic microscopy. Wikipedia. Archived Feb. 17, 2015. Last accessed Jul. 5, 2023 from <https://web.archive.org/web/20150217070233/https://en.wikipedia.org/wiki_Digital_holographic_microscopy.htm>. 12 pages.
[No Author Listed], Nikon. BioStation IM-Q product webpage. Archived Jan. 19, 2015. Last accessed Nov. 24, 2023 from <https://web.archive.org/web/20150119025735/http://www.nikon.com/products/instruments/lineup/bioscience/time/imq/index.htm>. 11 pages.
Buggenthin et al., An automatic method for robust and fast cell detection in bright field images from high-throughput microscopy. BMC Bioinformatics. Oct. 4, 2013;14:297.
Colomb et al., Advantages of digital holographic microscopy for real-time full field absolute phase imaging. Proceedings of SPIE. Feb. 2008; 6861:10 pages.
Rappaz et al., Digital holographic microscopy: a quantitative label-free microscopy technique for phenotypic screening. Comb Chem High Throughput Screen. Jan. 2014;17(1):80-8. doi: 10.2174/13862073113166660062.

* cited by examiner

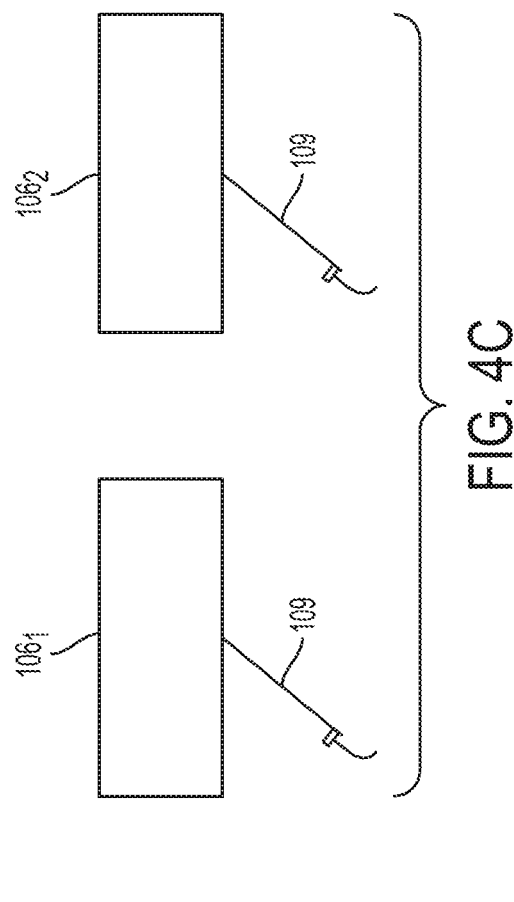
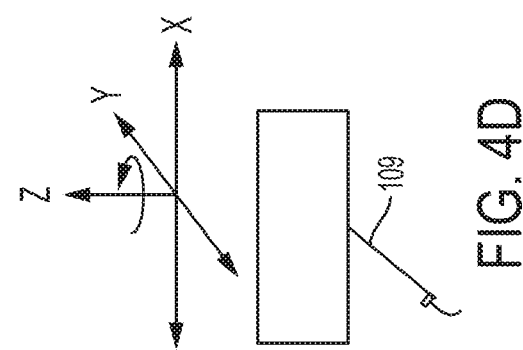
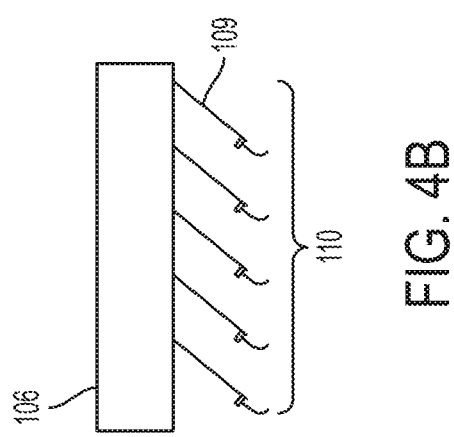

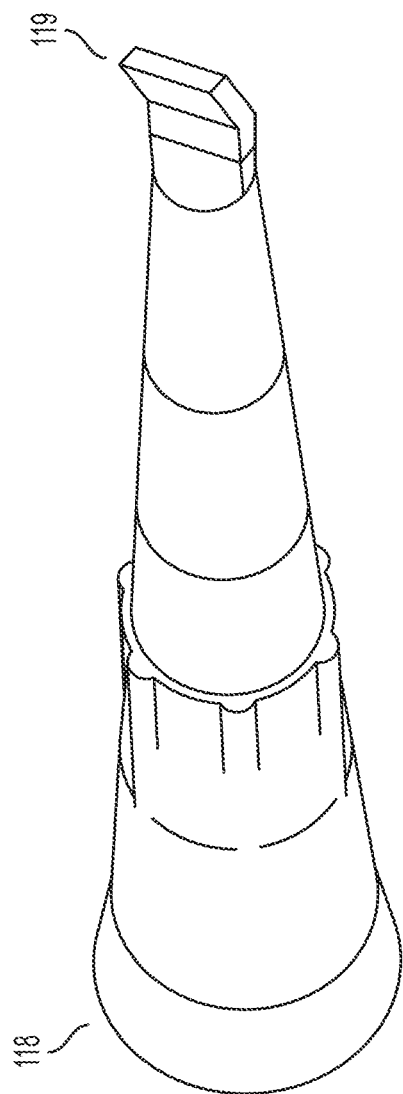
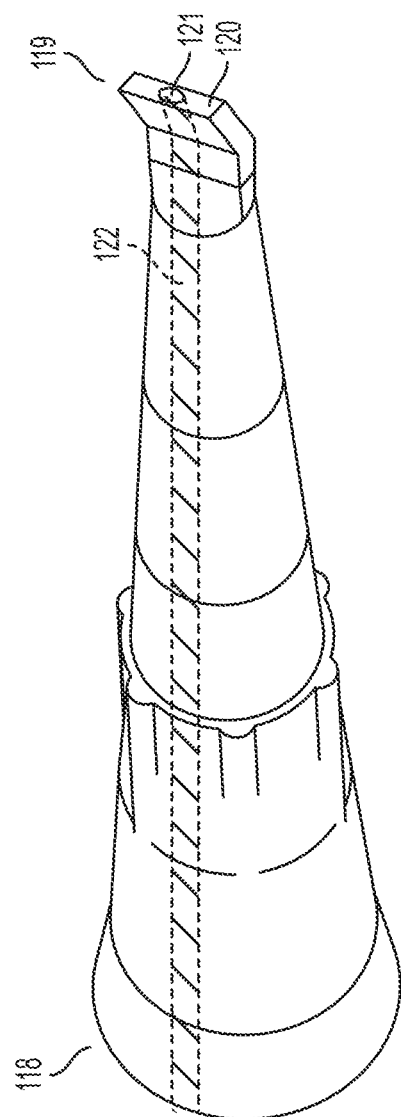
FIG. 5A
FIG. 5B

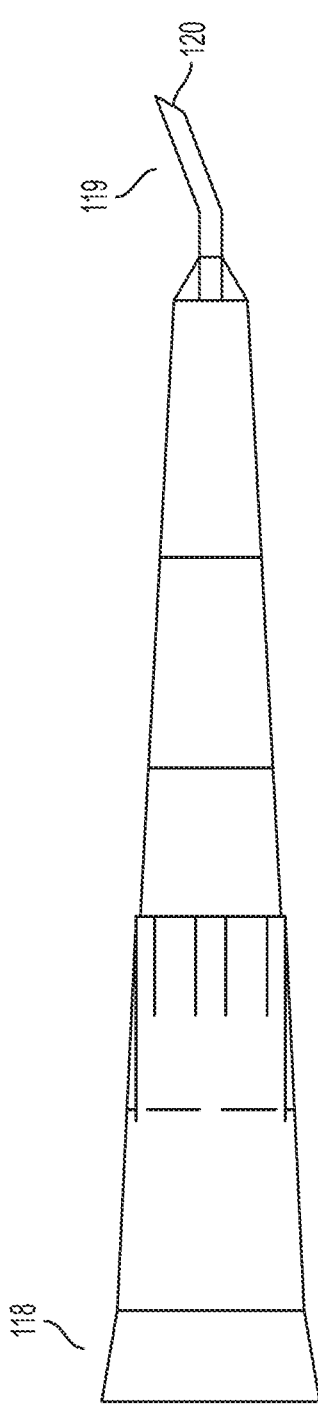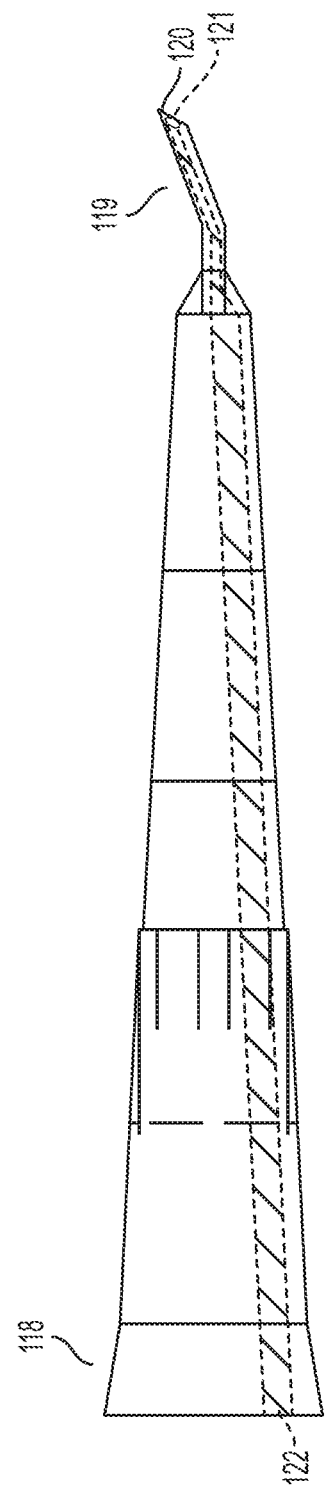

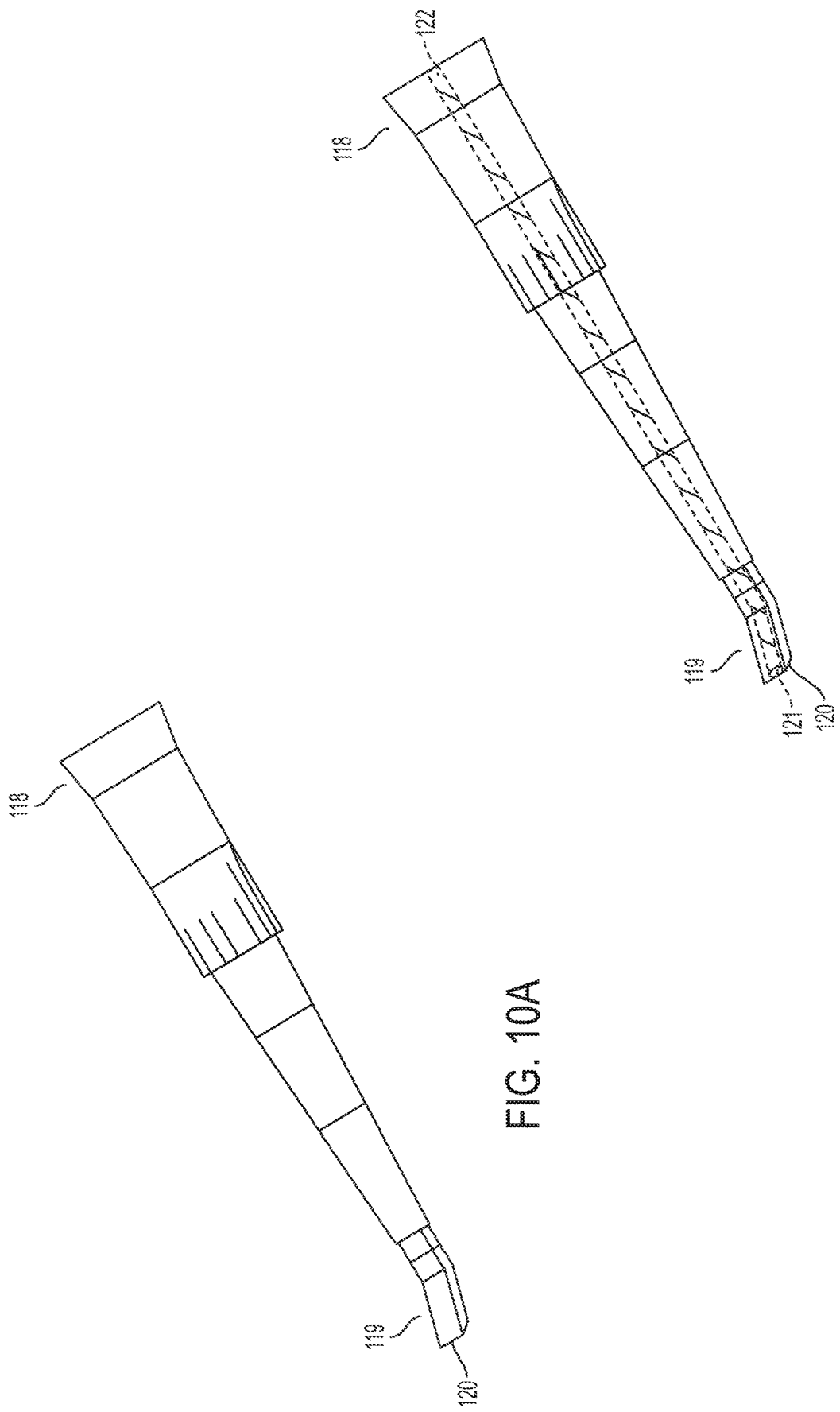

CELL CULTURE INCUBATORS WITH INTEGRATED CELL MANIPULATION SYSTEMS

RELATED APPLICATIONS

This application is a continuation of and claims priority under 35 U.S.C. § 120 to U.S. application Ser. No. 17/718,570, filed Apr. 12, 2022, now U.S. Pat. No. 11,920,122, which is a continuation of U.S. application Ser. No. 15/931,927, filed May 14, 2020, now U.S. Pat. No. 11,332,705, which is a continuation of and claims priority under 35 U.S.C. § 120 to U.S. application Ser. No. 15/563,383, filed Sep. 29, 2017, now, U.S. Pat. No. 10,696,937, which is a national stage filing under 35 U.S.C. § 371 of International Application No. PCT/US2016/025356, entitled "CELL CULTURE INCUBATORS WITH INTEGRATED CELL MANIPULATION SYSTEMS" and filed Mar. 31, 2016. International Application No. PCT/US2016/025356 claims the benefit under 35 U.S.C. 119 (e) of U.S. Provisional Application Ser. No. 62/141,191, filed Mar. 31, 2015 and entitled "Cell Culture Incubators With Integrated Cell Manipulation Systems". The entirety of each of the applications listed above is incorporated by reference herein.

FIELD

Aspects relate to cell culture incubators and to methods for using such incubators.

BACKGROUND

Cell culture is a useful technique in both research and clinical contexts. For example, culture of mammalian cells is often performed in order to establish clonal cell lines, tissue preparations, in vitro fertilization preparations or to expand populations of stem cells. However, maintenance of cell cultures in presently available cell incubators is a laborious process requiring highly trained personnel and stringent aseptic conditions. For example, to passage adherent cells at an appropriate degree of confluence, the adherent cells must be dissociated from the cell culture vessel in which they have been propagated and to which they have adhered. Typically, this process involves removing the cell culture vessel from a controlled environment (e.g., an incubator) to a cell culture hood and manually passaging the cells. This high level of human involvement can introduce contaminants into the culture or damage the cells, thereby lowering culture efficiency and repeatability.

SUMMARY

Presently available cell culture incubators impose several barriers to productive long-term cell culture. For example, many presently available cell incubators require the removal of culture plates from the incubator for manipulating cells. Generally, removing cell culture plates from an incubator increases the threat of contamination to the culture because upon removal, the culture is exposed to non-aseptic conditions and/or variations of the physical environment (e.g., changes in temperature, humidity, etc., or any combination thereof).

The instant document provides a cell culture system with an integrated manipulation device, e.g., having one or more cell scrapers, that can reduce the exposure of cultures to contaminants, the external environment and/or variations of the incubator environment by eliminating the need to remove culture vessels from the incubator for maintenance of cell cultures (e.g., passaging the cells).

Accordingly, in some aspects this document provides a cell culture incubator comprising: an incubator cabinet comprising an internal chamber for incubation of cells in one or more cell culture vessels, (e.g., wherein the internal chamber is configured to hold the one or more cell culture vessels); an external door opening from an external environment to the internal chamber; an imager (e.g., an imager and an imaging location), configured for imaging the cells within the internal chamber (e.g., when the one or more cell culture vessels are at the imaging location); a manipulator (e.g., a manipulator and a manipulating location) having one or more cell scrapers for manipulating the cells (e.g., dissociating adherent cells from the cell culture vessel, cleaning a cell culture vessel) in the one or more cell culture vessels within the internal chamber; and a cell culture vessel transfer device for moving the one or more cell culture vessels between locations within said internal chamber (e.g., from the imaging location to the manipulating location or from the manipulating location to the imaging location).

In some embodiments, the manipulator comprises one or more cell scrapers. In some embodiments, each cell scraper comprises a handle portion comprising a elongate member extending from a proximal region that is attachable or connectable with a manipulator base and a distal region that comprises a scraping edge. In some embodiments, each cell scraper comprises a contiguous structure (e.g., a molded structure) comprising a scraping edge. In some embodiments, each cell scraper comprises one or more interconnected parts. In some embodiments, each cell scraper comprises a handle having an interface for replaceably connecting a scraping edge assembly to the handle. Thus, in some embodiments, a disposable scraper edge is provided that is detachable or releasable from the scraper handle. In some embodiments, each cell scraper comprises a scraper edge contactable with the surface of a cell culture vessel and configured for scraping cells adhering to the surface without substantially killing the cells. In some embodiments, the incubator further comprises a controller configured for controlling the manipulator to modulate the contact pressure between a scraping edge of the cell scraper and the surface of a cell culture vessel. In some embodiments, the incubator further comprises a sensor connected to the cell scraper (e.g., a strain gauge sensor) that provides signal to a controller informative of a sensed pressure between a scraping edge of the cell scraper and the surface of a cell culture vessel, wherein the controller is configured to transmit a control signal to the manipulator to increase or decrease the pressure between a scraping edge of the cell scraper and the surface of a cell culture vessel in response to the sensed pressure. In some embodiments, each cell scraper is readily removable from the manipulator. In some embodiments, each cell scraper is configured to perform scraping and liquid handling functions. In some embodiments, each cell scraper comprises a scraping edge configured to allow a definable range of scraping edge deflection on contact with a cell culture vessel. In some embodiments, each cell scraper comprises one or more components formed from a polymer. In some embodiments, each cell scraper further comprises an opening configured for aspirating cells and/or cell culture media, wherein the opening is positioned in close proximity to a scraping edge.

In some embodiments, the cell scraper is disposable. In some embodiments, the cell scraper is configured to perform scraping and liquid handling functions. In some embodiments, the cell scraper comprises a scraping edge configured to allow a definable range of scraping edge deflection on contact with a cell culture vessel. In some embodiments, a scraping edge is formed from a polymer. In some embodiments, the edge comprises a geometry configured for excision of certain cells (e.g., pre-differentiated cells) from a larger population of cells (e.g., healthy stem cell colonies). In some embodiments, the scraping edge further comprises an opening (e.g., an orifice) configured for transporting (e.g., aspirating, depositing, or aspirating and depositing) cells and or cell culture media, wherein the opening (e.g., orifice) is positioned in close proximity to the scraping blade.

In some embodiments, an opening (e.g., orifice). In some embodiments, the opening is configured for transporting (e.g., aspirating, depositing, or aspirating and depositing) cells and/or cell culture media and forms part of (e.g., is connected to) a channel. In some embodiments, a channel is integrated into a cell scraper (e.g., running along the inside or outside of a cell scraper handle and/or scraping blade). In some embodiments, the incubator further comprises one or more additional manipulators, each having at least one cell scraper. In some embodiments, the at least one cell scraper (e.g., of the one or more manipulators) is at least 2, 3, 4, 5, 10, 15, 20, 50, 100, 200, 300, 500, or up to 1000 cell scrapers.

In some embodiments, the cell culture incubator further comprises a controller of the manipulator for manipulating the cells. In some embodiments, the controller of the manipulator is configured to quantify and modulate the contact force between the scraping edge and the surface of a cell culture vessel to which cells are adhered. In some embodiments, the controller is located exterior to the incubator cabinet. In some embodiments, the controller is inside or integrated into the incubator cabinet. In some embodiments, the controller comprises a computer.

In some embodiments, an imager is provided in the incubator cabinet. In some embodiments, the imager is configured to enable selective scraping of cells with the manipulator while imaging the cells to be scraped or that are scraped. In some embodiments, the imager is a holographic microscope. In some embodiments, the imager is a bright-field microscope. In some embodiments, the imager is a fluorescence microscope. In some embodiments, the imager is a phase-contrast microscope. In some embodiments, cell culture incubators further comprise a second imager, or a second imager and a third imager. In some embodiments, cell culture incubators having 3 imagers comprise a holographic microscope, a bright-field microscope, and a fluorescence microscope. In some embodiments, cell culture incubators having 3 imagers comprise a phase-contrast microscope, a holographic microscope, and a fluorescence microscope. In some embodiments, the imager is used to analyze the cells and determine automatically an area to be scraped. In other embodiments, the automatic selection of an area to be scraped is modified by an operator. In other embodiment, the operator selects manually an area to be scraped from the plurality of images acquired by the imagers.

In some embodiments, the one or more cell culture vessels are flasks, suspension culture flasks, spinner flasks, plates, petri dishes and/or bags. In some embodiments, the one or more cell culture vessels comprise fiducial marks for facilitating alignment of the one or more cell culture vessels to the imager and the manipulator.

In some embodiments, the manipulator for manipulating the cells is a cell picker. In some embodiments, the cell culture incubator further comprises a controller of the manipulator for manipulating the cells. In some embodiments, when the one or more cell culture vessels are moved from an imaging location to a manipulating location or from a manipulating location to an imaging location, the one or more cell culture vessels are substantially aligned.

In some aspects, this document provides a cell culture incubator comprising: an incubator cabinet comprising an internal chamber for incubation of cells in one or more cell culture vessels, wherein the internal chamber is configured to hold the one or more cell culture vessels; a door opening to the internal chamber; a holographic imager comprising a first imaging location, the holographic imager configured for imaging the cells within the internal chamber when the one or more cell culture vessels are at the first imaging location; a second imager comprising a second imaging location, the imager configured for imaging the cells within the internal chamber when the one or more cell culture vessels are at the second imaging location; a manipulator for manipulating the cells in the one or more cell culture vessels at the second imaging location; and a cell culture vessel transfer device for moving the one or more cell culture vessels from the first imaging location to the second imaging location or from the second imaging location to the first imaging location.

In some embodiments, the holographic imager is a holographic microscope. In some embodiments, the second imager is a bright-field microscope. In some embodiments, the second imager is a fluorescence microscope. In some embodiments, cell culture incubators further comprise a third imager. In some embodiments, cell culture incubators comprise three imagers. In some embodiments, cell culture incubators having three imagers comprise a holographic microscope, a bright-field microscope, and a fluorescence microscope.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which:

FIG. 2A shows a schematic of a cell culture incubator having a second imager; FIG. 2B shows a schematic of a cell culture incubator, wherein the imaging location and the manipulating location are the same location; and, FIG. 3 is a schematic depicting further components of cell culture incubators.

FIGS. 4A-4D are schematics of illustrative embodiments of cell culture incubators; FIG. 4A shows a schematic of a cell culture incubator having a manipulator comprising a cell scraper;

FIG. 4B shows a schematic of a manipulator comprising a plurality of cell scrapers; FIG. 4C is a schematic of two manipulators, each manipulator comprising a cell scraper; FIG. 4D is a schematic depiction of the range of motion along x-, y- and z-axes of a manipulator comprising a cell scraper.

FIGS. 5A-5B are schematics of illustrative embodiments of cell scrapers. FIG. 5A shows a schematic of a cell scraper having a proximal end and a distal end comprising a scraper blade.

FIG. 5B shows a schematic of a cell scraper having a scraper blade comprising an opening and a channel (e.g., for aspirating cells and/or cell culture media).

FIG. 6A shows a side view schematic of a cell scraper having a proximal end and a distal end comprising a scraper blade. FIG. 6B shows a side view schematic of a cell scraper having a scraper blade comprising an opening and a (e.g., channel for aspirating cells and/or cell culture media).

FIGS. 7A-7B are schematics of illustrative embodiments of cell scrapers. FIG. 7A shows a side view schematic of a cell scraper having a proximal end and a distal end comprising a scraper blade. FIG. 7B shows a side view schematic of a cell scraper having a scraper blade comprising an opening and a (e.g., channel for aspirating cells and/or cell culture media).

FIG. 8A shows a back view (e.g., proximal to distal) schematic of a cell scraper having a proximal end and a distal end comprising a scraper blade. FIG. 8B shows a back view (e.g., proximal to distal) schematic of a cell scraper having a scraper blade comprising an opening and a channel (e.g., for aspirating cells and/or cell culture media).

FIG. 9A shows a schematic of a cell scraper having a proximal end and a distal end comprising a scraper blade.

FIG. 9B shows a schematic of a cell scraper having a scraper blade comprising an opening and a channel (e.g., for aspirating cells and/or cell culture media).

FIGS. 10A-10B are schematics of illustrative embodiments of cell scrapers. FIG. 10A shows a schematic of a cell scraper having a proximal end and a distal end comprising a scraper blade. FIG. 10B shows a schematic of a cell scraper having a scraper blade comprising an opening and a channel (e.g., for aspirating cells and/or cell culture media).

FIG. 15B shows a front view schematic of a scraper blade. FIG. 15C shows a side view schematic of a scraper blade.

DETAILED DESCRIPTION

Figure 1:
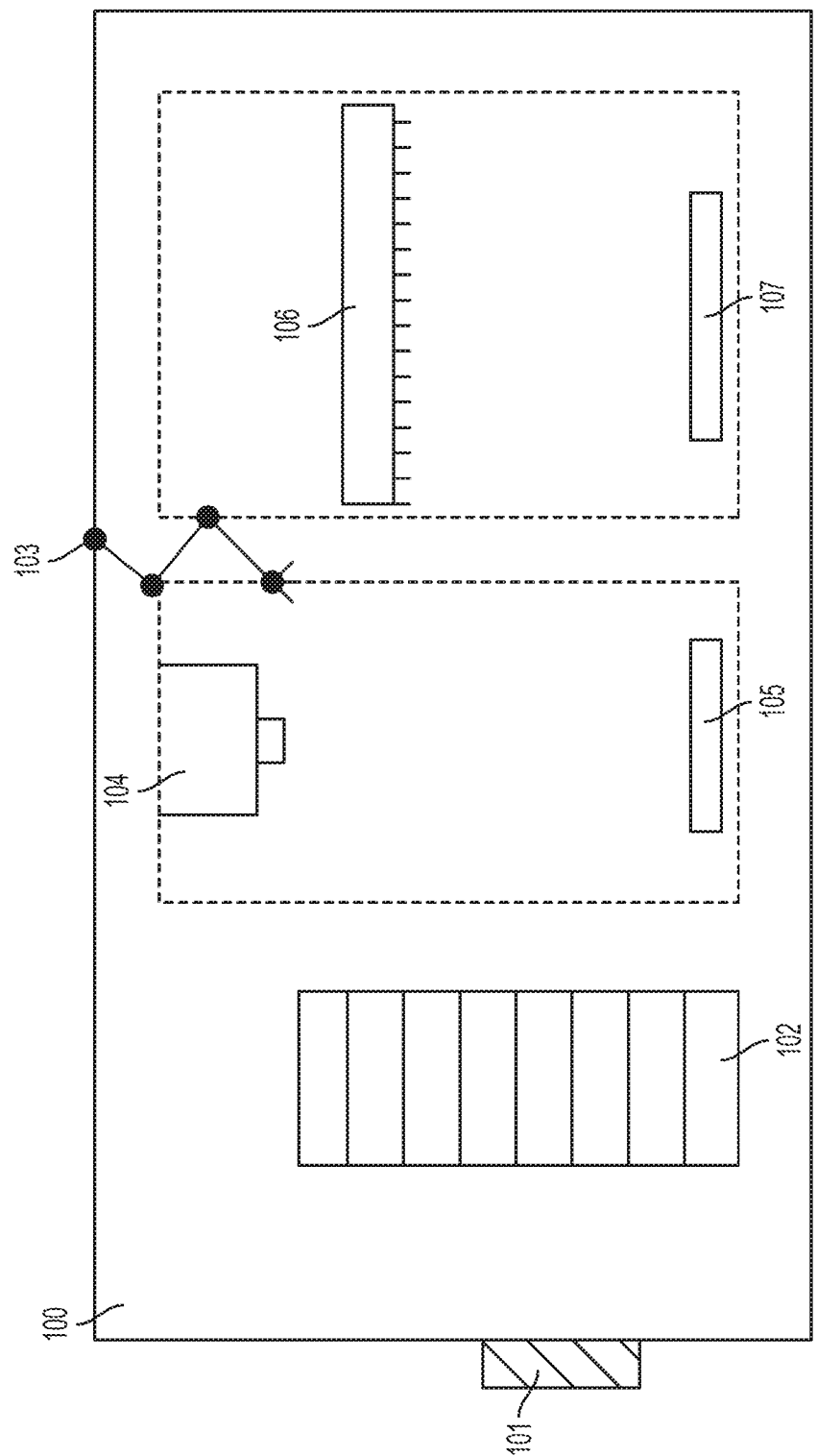
FIG. 1 is a schematic of an illustrative embodiment of a cell culture incubator having an imager and a manipulator.

Currently used cell culture incubators impose barriers to the success of cell cultures. For example, many cell culture incubators require the removal of cell culture vessels and their subsequent manual handling for imaging and manipulating of the cultured cells. Removal of cultured cells from the protected environment provided by the incubator increases exposure of the culture to potential contaminants and to environmental changes that may interfere with cell growth. In some cases, removal of cultures from the incubator exposes laboratory personnel to pathogenic organisms being cultured in the incubator. Furthermore, manual handling of cultures by human operators introduces the possibility of contamination introduced by human error, such as improper sterile technique. This document provides cell culture incubators having an integrated manipulator device (e.g., incubators comprising a cell scraper).

In some aspects, this document relates to a cell culture incubator having: an incubator cabinet comprising an internal chamber for incubation of cells in one or more cell culture vessels, wherein the internal chamber is configured to hold the one or more cell culture vessels; an external door opening from an external environment to the internal chamber; an imager and an imaging location, the imager configured for imaging the cells within the internal chamber when the one or more cell culture vessels are at the imaging location; a manipulator and a manipulating location for manipulating the cells in the one or more cell culture vessels within the internal chamber; and a cell culture vessel transfer device for moving the one or more cell culture vessels from the imaging location to the manipulating location or from the manipulating location to the imaging location. In some embodiments, the manipulator comprises one or more cell scrapers.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a compressed gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator cabinet), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., barcode readers, cameras, etc.), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator, but are external to the incubator cabinet. In some embodiments, one or more of these other elements are included within the incubator cabinet.

As used herein, an "internal chamber" is a chamber disposed in an incubator cabinet. An internal chamber may include one or more windows (e.g., optical windows made of glass, plastic, composite, or other substantially transparent material for viewing an area inside the incubator cabinet). An internal chamber may include at least one door (e.g., for permitting the transfer of items into or out of the internal chamber). In some embodiments, the at least one door may be disposed between the internal chamber and a transfer chamber. In certain embodiments, an interlock may prevent the door from opening at an undesirable time (e.g., when a portion of the incubator cabinet is open to the surrounding environment so that contaminants cannot enter the internal chamber). An internal chamber may be of any appropriate size and geometry. In some embodiments, an incubator cabinet may include more than one internal chamber. In other embodiments, an internal chamber may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources. In some embodiments, an internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

An internal chamber may be made of any useful material. In some embodiments, an internal chamber may include one or more plastics, polymers, metals, or glasses.

As used herein, a "door" is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

A transfer device for moving one or more items may be used to move items between the transfer chamber and the internal chamber. In some embodiments, the transfer device comprises a conveyor belt or other similar device for maneuvering items. Non-limiting examples of items that can be moved by transfer devices include cell culture vessels, pipettes, containers, syringes and other materials and instruments utilized in the culture of cells. In some embodiments, more than one transfer device may be included. In some embodiments, one or more transfer devices are located in the transfer chamber and/or in the internal chamber. In some embodiments, a transfer device may include one or more robotic elements. For example, a transfer device may comprise include one or more robotic arms capable of gripping, lifting, pushing, grabbing, sliding, rotating, translating, releasing, raising, lowering, and/or tilting one or more items (e.g., pipettes).

In some embodiments, the transfer device is a cell culture vessel transfer device. As used herein, a "cell culture vessel transfer device" refers to a device that can transfer one or more cell culture vessels from a first location to a second location. In some embodiments, the transfer device is anchored within the internal chamber. In certain embodiments, the transfer device may transfer one or more items to or from multiple locations in an incubator cabinet. For example, a cell culture vessel transfer device may be used to move a cell culture vessel from a transfer chamber to an internal chamber, and/or from a storage location to an imaging location. In some embodiments, an incubator cabinet includes more than one transfer device for moving one or more items (e.g., separate means for transferring items between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In some cases, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator cabinet (e.g., within a storage array in an internal chamber).

In some embodiments, a cell culture vessel transfer device is an automated transfer device. For example, the automated transfer device may be a robotic arm controlled by a computer that is programmed to move cell culture vessels from a storage location within the internal chamber of the incubator to an imaging location within the internal chamber of the incubator. In some embodiments, a cell culture vessel transfer device is manually operated. For example, a robotic arm located inside the internal chamber of an incubator may be operated by a user-controlled joystick from a location outside of the internal chamber of the incubator in order to move cell culture vessels from a storage location within the internal chamber of the incubator to an imaging location within the internal chamber of the incubator.

As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. Non-limiting examples of cell culture vessels include flasks, suspension culture flasks, spinner flasks, plates, petri dishes and/or bags. In certain embodiments, a cell culture vessel includes a transparent or optically clear window. For example, a lid coupled to the housing of a cell culture vessel may include an optically clear portion for viewing cells e.g., with a microscope or other imager. In some embodiments, a cell culture vessel includes one or more portions that are substantially non-reflective. In some embodiments, the cell culture vessel is barcoded. Therefore, in some embodiments, the incubator includes a barcode reader.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80° C. and about 37° C. In some embodiments, pre-kitted cell culture storage vessels are stored prior to use at temperatures between about −80° C. and about −20° C. In some embodiments, pre-kitted cell culture storage vessels are stored prior to use at temperatures between about −20° C. and about 4° C. In some embodiments, pre-kitted cell culture storage vessels are stored prior to use at temperatures between about 4° C. and about 37° C. In some embodiments, pre-kitted cell culture vessels are disposable. In some embodiments, pre-kitted cell culture vessels are reusable and/or refillable.

As used herein, a "storage location" refers to a location at which one or more cell culture vessels is stored (e.g., within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that are molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device camera or CMOS camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence imager or microscope. In other embodiments, the imager is a phase-contrast microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator cabinet provided herein.

As used herein, a "phase-contrast microscope" is an imager that converts phase shifts in light passing through a transparent specimen to brightness changes in the image. Phase shifts themselves are invisible, but become visible when shown as brightness variations. Any appropriate phase-contrast microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes, or two phase-contrast microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope. In some embodiments, cell culture incubators having 3 imagers comprise a phase-contrast microscope, a holographic microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

In some embodiments, a cell culture vessel is substantially aligned with an imager. In some embodiments, a cell culture vessel is substantially aligned with an imager via the use of at least one fiducial mark. As used herein, the term "substantially aligned" implies that one or more elements are substantially overlapping, identical, and/or in line with one another. The substantial alignment of one or more cell culture vessels at one or more locations (e.g., imaging locations) may facilitate the analysis of a sample by permitting overlapping images of the cell culture vessel to be obtained. For example, a cell culture vessel may be imaged at a first imaging location by a first imager and subsequently imaged at a second imaging location by a second imager. If the imaging fields of the respective imagers are substantially aligned, the images recorded by the first and second imagers may be combined ("stitched together") for analysis. One or more fiducial marks present on one or more cell culture vessels may facilitate substantial alignment. In some cases, one or more fiducial marks present at one or more imaging or other locations (e.g., manipulation or maintenance locations) may facilitate substantial alignment.

As used herein, a "manipulator for manipulating cells" refers to a device for manipulating cells in the internal chamber. The manipulator may include one or more needles, capillaries, pipettes, and/or micromanipulators. In some embodiments, a manipulator comprises one or more cell scrapers. As used herein, "cell scraper" refers to a device comprising a scraping edge suitable for scraping cells off of a surface. In some embodiments, a cell scraper comprises a handle portion comprising a elongate member extending from a proximal region that is attachable or connectable with a manipulator base and a distal region that comprises a scraping edge. In some embodiments, a cell scraper is a contiguous structure (e.g., a molded structure) comprising a scraping edge. However, in some embodiments, a cell scraper comprises one or more interconnected parts. For example, in some embodiments, a cell scraper comprises a handle having an interface for replaceably connecting or attaching a scraping edge or scraping edge assembly to the handle. In some embodiments, the scraping edge is a portion of a cell scraper contactable with the surface of a cell culture vessel or other surface and suitably configured for scraping matter from the surface for cleaning the surface and/or for scraping cells adhering to the surface without substantially killing the cells, e.g., by mechanically lysing the cells. In some embodiments, it is desirable for a scraping edge or scraping edge assembly to be disposable in order to prevent cross-contamination between cell cultures. Thus, in some embodiments, the scraping edge or scraping edge assembly is disposable.

In some embodiments, a scraping edge comprises a blade, wiper or an otherwise substantially planar surface comprising an edge (e.g., a beveled edge) that is configured for removing cells from the surface of a cell culture vessel when pushed or pulled along the surface of the cell culture vessel. In some embodiments, a scraping edge can be made of a polymer or combination of polymers (e.g., plastic, silicone), glass, metal or any other suitable material. However, in some embodiments, the scraping edge comprises mechanical/material properties that allow for a definable range of scraping edge deflection on contact, which allows for close control of angle of contact with the cell culture vessel surface/adherent cells. In some embodiments, edge of the cell scraper is formed from a polymer. Examples of polymers used to form scraping edge include, but are not limited to, silicone, polyurethane, polyethylene, polyester, polypropylene, polybutylene, polystyrene, polyvinyl chloride (PVC), and nylon. In some embodiments, a blade comprises a geometry configured for excision of certain cells (e.g., pre-differentiated cells) from a larger population of cells (e.g., healthy stem cell colonies).

In certain embodiments, a cell scraper is configured to perform scraping and liquid handling functions. For example, in some embodiments a scraper further comprises an opening(s) (e.g., orifice(s)) in close proximity to a scraping edge (e.g., blade) together with an accompanying port to a pipet head or other fluid movement device (e.g., a pump, vacuum chamber), thus allowing simultaneous scraping and aspiration of cellular material. Such a configuration is useful, in some embodiments, for the option for cell cleaning or colony picking (e.g., in the context of stem cells separation).

In some embodiments, an opening (e.g., orifice) configured for transporting (e.g., aspirating, depositing, or aspirating and depositing) cells and/or cell culture media forms part of a channel. As used herein, a "channel" refers to a partially enclosed conduit (e.g., a cylindrical, tubular, or cuboid passage) designed to allow the transport of a objects (e.g., cell culture media, cells) from one location to another location. In some embodiments, a channel is integrated into a cell scraper (e.g., running along the inside or outside of a cell scraper handle and/or scraping blade). For example, in some embodiments, a cell scraper comprises a hollow handle configured to contain a channel comprising an opening, wherein the opening is located in or on the scraping blade (e.g., scraping edge) of the cell scraper. A channel residing within the interior of a hollow scraper handle (e.g., in a scraper handle cavity) can have a volume ranging from about 0.1% of the volume within the handle cavity to about 99% of the volume within the handle. For example, a channel can be a separate capillary tube or hollow needle (e.g., a needle having a gauge between 28 gauge and 10 gauge) that is directly connected or attached to a wall (e.g., running along an interior wall or exterior wall) of a hollow scraper handle. In some embodiments, the entire volume within a hollow scraper handle forms a channel. For example, in some embodiments, a cell scraper comprises a hollow handle and a scraper blade having an opening which is connected to the hollow interior (e.g., channel) of the handle. In some embodiments internal structures such as a mesh, grill, screen, or star-shaped structure, to facilitate the mixing or breaking apart of aggregated cells, are integrated into the channel of a cell scraper handle and/or scraping blade. Without wishing to be bound by any particular theory, a cell scraper comprising an opening and a channel is capable of simultaneously performing cell scraping and liquid handling functions (e.g., simultaneously triturating cells and removing debris, such as triturated cells and cell culture media).

In some embodiments, a manipulator comprises at least one cell scraper. For example, a manipulator may comprise between about 1 and about 100, about 10 and about 100, about 20 and about 1000, or about 50 and about 500 cell scrapers. In some embodiments, a manipulator comprises 2, 3, 4, 5, 6, 7, 8, 9, 10, 15, 20, 24, 48, 96, 384, or 1536 cell scrapers. In some embodiments, a manipulator having a plurality of cell scrapers is referred to as having a "bank" of cell scrapers, as shown in FIG. 4B. In some embodiments, a manipulator comprises a single cell scraper. In some embodiments, an incubator may comprise multiple manipulators, each manipulator having at least one cell scraper (e.g., as depicted in FIG. 4C).

In some embodiments, cell scrapers are useful for dissociating adherent cells from the surface (or surfaces) of a cell culture vessel. For example, cell scrapers may be utilized for manual, mechanical loosening of protein bonds of adherent cells to a culture vessel. In some instances, mechanical dissociation by scraping is aided by the use of an enzyme such as trypsin or ACCUTASE®. However, in certain embodiments, cell scraping is the preferred method of cell dissociation, primarily because the use of enzymes as the primary means of dissociation requires relatively long exposure of the cells to the enzyme in order to insure sufficient cellular detachment from the substrate. In some embodiments, scraping is the preferred methods for passaging stem cells during expansion.

A manipulator may include a cell picker. A manipulator for manipulating cells may operate by detecting desirable cells or groups thereof present at a first location based on a predetermined criterion and transferring the desired cells or groups thereof from the first location to a second location. A cell picker may detect, pick, and/or transfer desirable or undesirable (e.g., pre-differentiated cell weeding) cells or groups thereof based on a manual or automated analysis. In some embodiments, information produced by an imager may be analyzed to detect desirable or undesirable cells. The cell picker may then transfer the desirable or undesirable cells to the second location. For example, an imager may image cells in or on a cell culture vessel at an imaging location, and the image used to identify desirable or undesirable cells or groups thereof. The cell picker may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the first location of the cells may be in or on a cell culture vessel. In particular embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, the manipulator includes at least one microelectrode. As used herein, the term "microelectrode" refers to an electrical conductor used to deliver electrical stimulation to a cell. For example, microelectrodes can be used to deliver genetic material into a cell by electroporation. In some embodiments, the manipulator includes at least one microinjector. Generally, microinjectors are glass micropipettes that have been pulled to form a sharp, hollow structure capable of piercing the membrane of a cell and serving as a conduit for the introduction of genetic material into the cell.

In some embodiments, a manipulator is manually operated. For example, a manipulator having a cell picker located inside the internal chamber of an incubator cabinet may be electronically-linked to and controlled by a user-directed joystick located outside the internal chamber of the incubator cabinet. In some embodiments, the user-directed joystick is connected to a display device. In some embodiments, the display device shows images captured by an imaging device inside the internal chamber of the incubator cabinet.

In some embodiments, a manipulator is automated. For example, a manipulator inside an internal chamber of an incubator cabinet may be electronically connected to a controller outside of the incubator cabinet, which is electronically connected to a computer that directs the manipulator. In some embodiments, a controller interfaces with hardware configured for quantifying and modulating contact force between a scraping edge and the surface of the cell culture vessel to which the cells are adhered. For example, a manipulator or cell scraper may further comprise a sensor (e.g., a pressure sensor) that provides signal to a controller informative of a sensed pressure, which in response to the controller transmits a signal (e.g., to a manipulator) to increase or reduce the pressure which the manipulator exerts upon the scraping edge (e.g., a blade) of the cell scraper. In some embodiments, a controller comprises software and/or hardware configured for programming up to 360° rotation of the scraper tip/blade, thus allowing for programming of scraping motion in coordination with linear motion in the x-, y-, and z-axis such that a constant angle of attack is maintained between the scraper blade and the cells being scraped, regardless of culture vessel well geometry. In some embodiments, the controller interfaces with one or more components or hardware configured to permit location and determination, e.g., via imaging, of aggregated clump(s) of cells, thus allowing subsequent scraping/aspiration via the manipulator-controlled cell scraper.

One or more elements of the manipulator for manipulating cells may be sterilized, for example using a sterilizing composition or method (e.g., ethanol or ozone gas, UV Light, Hydrogen peroxide), prior to manipulation.

As used herein, "manipulation location" refers to the location at which cells are manipulated by a manipulator for manipulating cells (e.g., a cell picker). In certain embodiments, the manipulation location may be the same as the imaging location.

According to one aspect, the cell culture incubator includes an incubator cabinet with an imaging location and a manipulating location. Cells of a cell culture vessel are imaged at the imaging location by an imager and manipulated at the manipulating location by a manipulator. In some embodiments, the imaging location and the manipulating location are two distinct locations within the incubator cabinet. The cell culture incubator may include a transfer device that moves cell culture vessels between the imaging location and the storage location. In other embodiments, the imaging location and the manipulating location are the same, such that the cells of culture vessels are imaged at the manipulation location.

In some embodiments, an imager may be used in conjunction with a manipulator. For example, an imager may image cells in or on a cell culture vessel at an imaging location, and the image used to identify desirable cells or groups thereof. The cell picker, which may or may not be resident at the imaging location, may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, a single location within the incubator cabinet may serve as an imaging location and a manipulating location. In one embodiment, cells are imaged as they are manipulated by the manipulator. In some embodiments, the imaging location and imaging location may be at separate locations within the incubator cabinet.

In some embodiments, the manipulator includes sensors that allow it to report its position and determine when it has touched the bottom of the cell culture vessel. In some embodiments, an imager may be used to guide the manipulator in order to achieve repeatability and accuracy. In some embodiments, compliance (e.g., springiness) in the manipulator may be used to relax the need for extreme mechanical accuracy.

Turning to the figures, FIG. 1 depicts one illustrative embodiment of a cell culture incubator. The cell culture incubator includes an incubator cabinet having an internal chamber (100) for incubation of cells in one or more cell culture vessels. The incubator cabinet includes an external door (101) that opens and closes to permit communication between an external environment and the incubator cabinet. In some embodiments, the external door opens and closes to permit communication between an external environment and the internal chamber. The internal chamber is configured to hold one or more cell culture vessels. The one or more cell culture vessels are stored in a storage location (102). In some embodiments, the storage location is a free-standing structure. For example, a storage location may be a test tube or culture flask rack that can be removed from the internal chamber of the incubator for loading and unloading of culture vessels. In some embodiments, the storage location is affixed to a surface of the internal chamber. For example, the storage location may be a series of racks or shelves that are connected to the walls or floor of the internal chamber and are thus not able to be removed from the incubator cabinet.

In some embodiments, the cell culture incubator includes a cell culture vessel transfer device (103) for moving one or more cell culture vessels. The cell culture transfer device may be affixed to any appropriate surface of the internal chamber of the incubator. For example, the cell culture vessel transfer device may be affixed to the top or ceiling of the internal chamber. Alternatively, the cell culture vessel transfer device may be affixed to a side wall of the internal chamber. In some embodiments, the cell culture vessel transfer device is not affixed to the wall of the internal chamber. For example, the cell culture vessel transfer device may rest on a wheeled tripod or other mobile structure that can be moved around the internal chamber.

In some embodiments, the transfer device moves one or more cell culture vessels from a storage location (102) to an imaging location (105) or to a manipulation location (107). The transfer device (103) can also move one or more cell culture vessels from an imaging location (105) to a manipulation location (107) or from a manipulation location (107) to an imaging location (105). When imaging or manipulation are complete, the transfer device (103) moves one or more cell culture vessels from an imaging location (105) or a manipulation location (107) to a storage location (102).

In some embodiments, the incubator cabinet includes a first imaging location (105) and a manipulation location (107). In some embodiments, one or more imaging locations are located on a surface of the internal chamber opposite from an imager. In some embodiments, imaging locations are platforms, either free-standing or affixed to a surface of the internal chamber. In some embodiments, the platform is movable. For example, a movable platform may be affixed to two or more rods that allow the platform to be moved left, right, forward, backward, up or down in relation to an imager. In some embodiments, the movable platform is motorized.

In some embodiments, the incubator cabinet includes a first imager (104) that images the cells of cell culture vessels when the vessels are at the first imaging location (105). In some embodiments, the first imager is a bright-field microscope. In some embodiments, the first imager is a holographic microscope. In some embodiments, the first imager is a phase-contrast microscope.

In some embodiments, a manipulator (106) manipulates the cells of cell culture vessels when the vessels are at the manipulation location (107). In some embodiments, the manipulator has an array of needles, capillaries, pipettes, and/or micromanipulators. For example, the manipulator may include a cell picker. In some embodiments, a manipulator comprises one or more cell pickers. In some embodiments, the manipulator may include a cell scraper. In some embodiments, a manipulator comprises one or more cell scrapers. Generally, manipulation locations share many characteristics with imaging locations, as described herein.

Figure 2A:
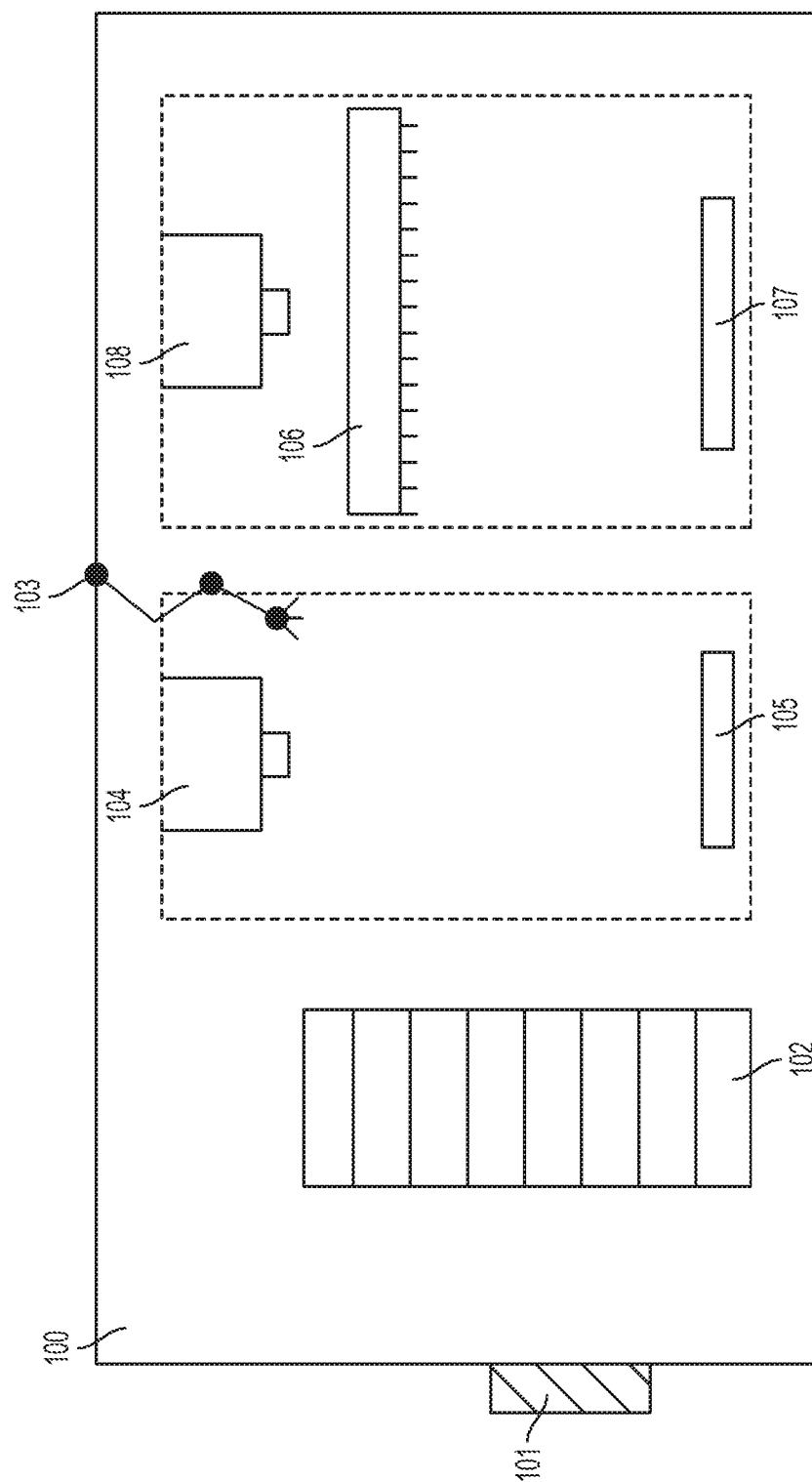
FIGS. 2A-2B are schematics of illustrative embodiments of cell culture incubators.

FIG. 2A depicts one illustrative embodiment of a cell culture incubator. In some embodiments, the incubator cabinet has a second imager (108). The second imaging location may be at or near the manipulation location (107). In some embodiments, the second imaging location and the manipulation location (107) are the same location. In some embodiments, a second imager (108) images the cells of cell culture vessels while the cells are manipulated by the manipulator (106). In some embodiments, the second imager is a brightfield microscope. In some embodiments, the second imager is a holographic microscope. In some embodiments, the first imager is a phase-contrast microscope.

Figure 2B:
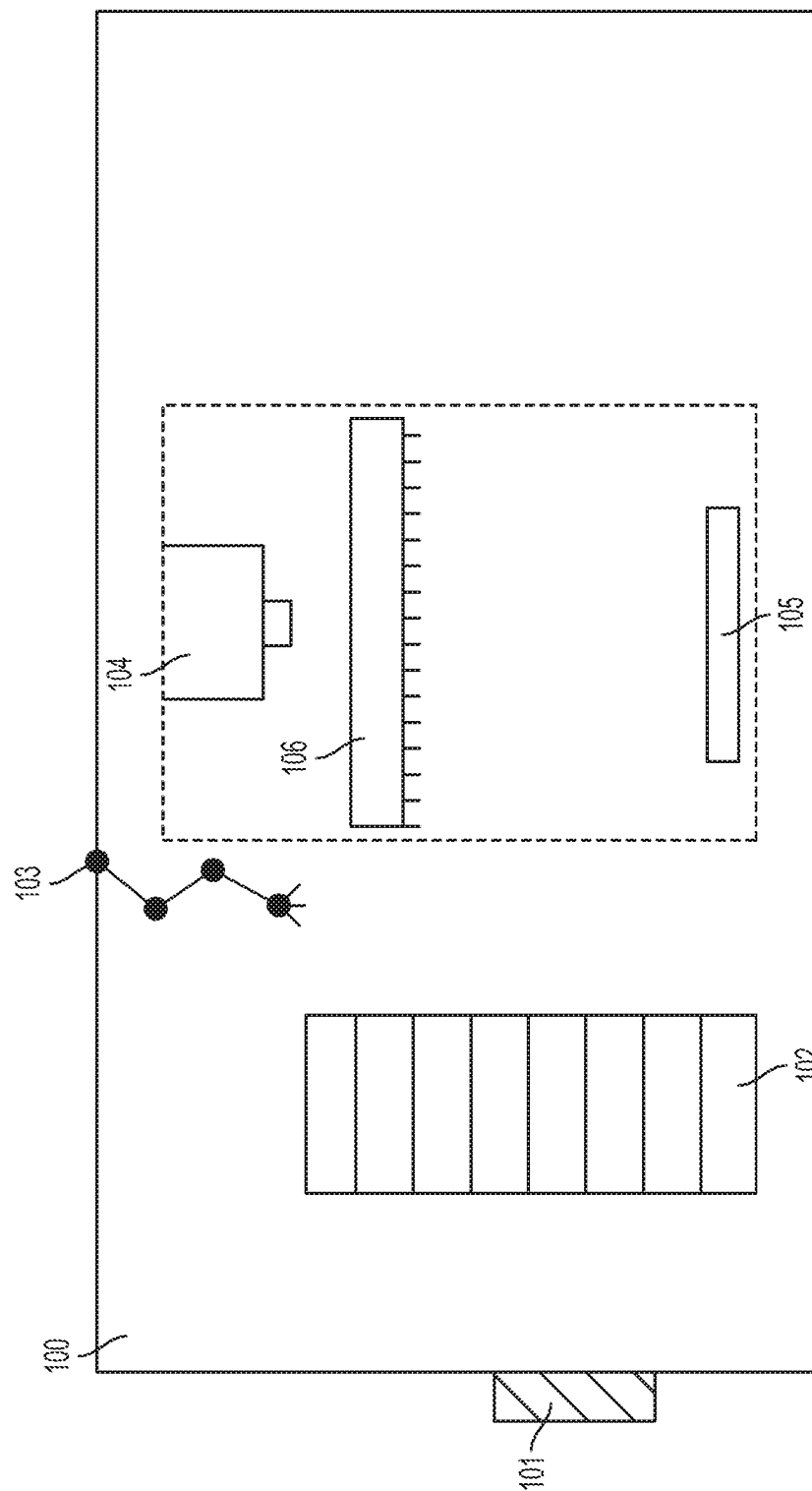

FIG. 2B depicts one illustrative embodiment of a cell culture incubator. In some embodiments, the cell culture incubator has an imaging location and a manipulation location that are the same location (105).

Figure 3:
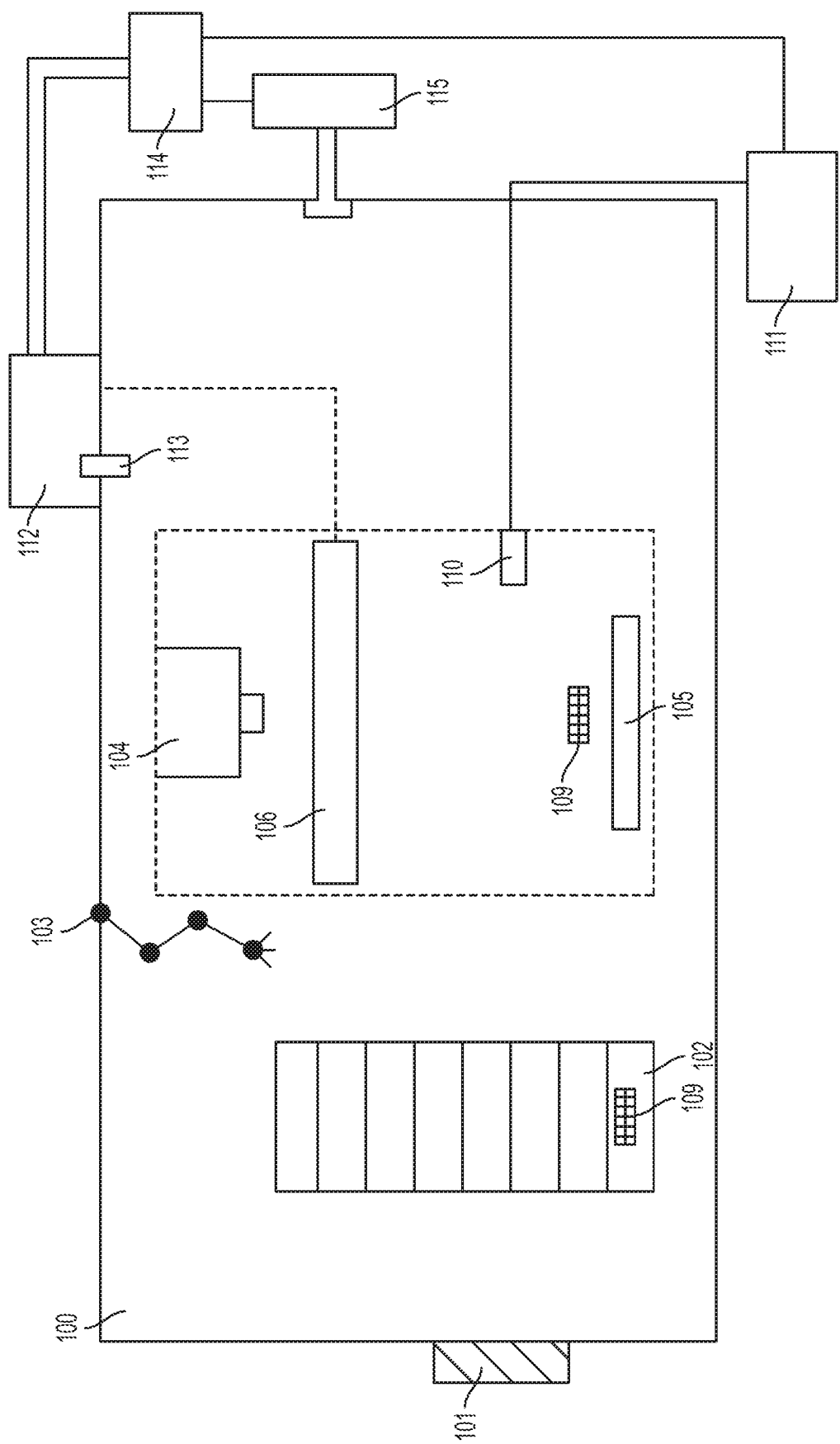

FIG. 3 depicts illustrative embodiments of further components of a cell culture incubator. Further components are any component of the incubator that is not listed in FIG. 1-2A or 2B. In some embodiments, a cell culture incubator contains barcoded cell culture vessels (109). Thus, in some embodiments, a cell culture incubator has a barcode scanner (110) located inside the internal chamber of the incubator cabinet. In some embodiments, the barcode reader communicates with a computer (111) to relay information about the cell culture vessel for which the barcode has been scanned. In some cases, a barcode scanner may be affixed to any surface of the internal chamber. For example, a barcode scanner can be affixed to a wall of the internal chamber in close proximity to an imaging location (105).

In some embodiments, the cell culture incubator contains at least one probe and/or at least one sensor (113) that measures environmental conditions within the internal chamber. Examples of probes to measure environmental conditions include but are not limited to temperature probes, pressure probes, carbon dioxide ($CO_2$) sensors, oxygen ($O_2$) sensors and relative humidity sensors. In some embodiments, the at least one probe and/or at least one sensor located within an instrument housing (112). The at least one probe and/or at least one sensor is connected to a controller (114). In some embodiments, the controller (114) communicates with a computer (111). Additionally, the controller (114) may communicate with a fluid dispensing system (115). For example, if a $CO_2$ sensor indicates a low $CO_2$ level in the internal chamber, the controller (114) may direct the fluid dispensing system (116) to inject $CO_2$ gas into the internal chamber in order to increase the $CO_2$ level of the internal chamber.

Figure 4A:
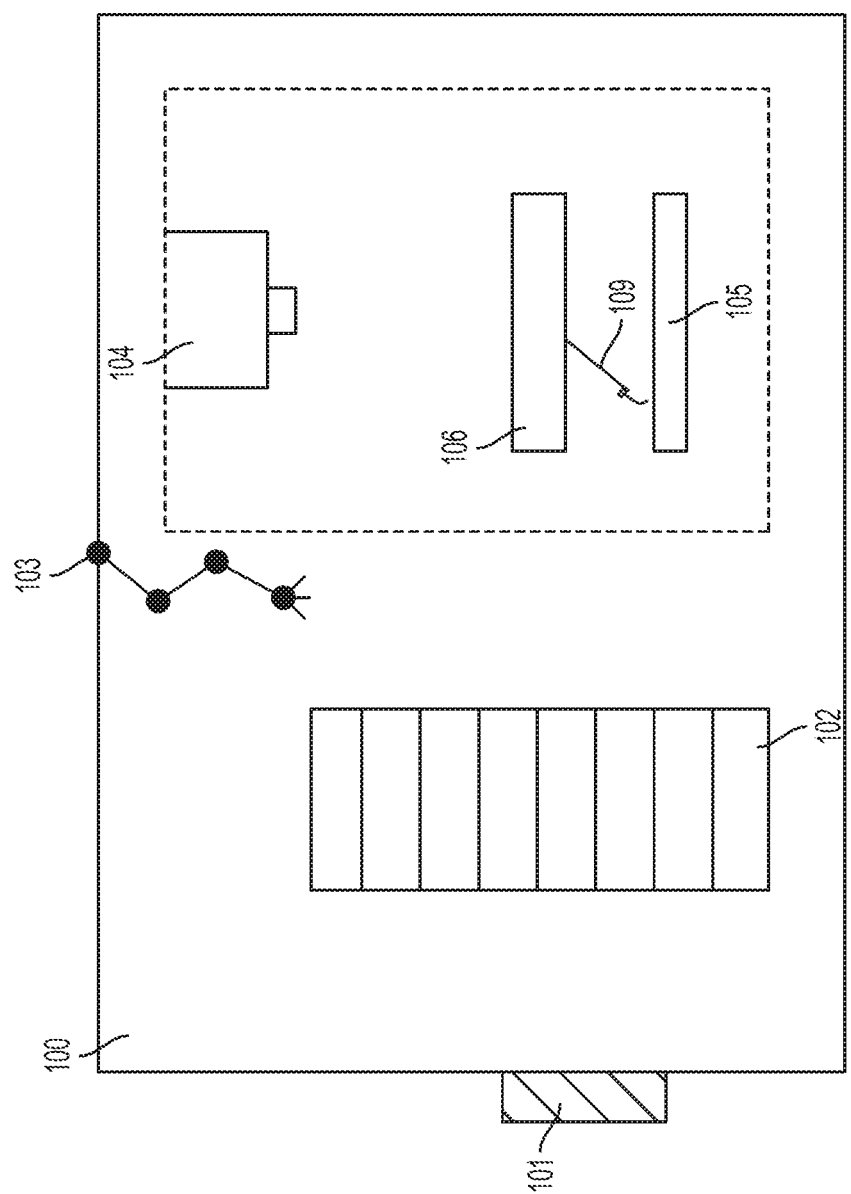

FIG. 4 depicts schematics of illustrative embodiments of cell culture incubators. In some embodiments, a manipulator (106) comprises one or more cell scrapers (116), as shown in FIG. 4A. In some embodiments, a manipulator (106) comprises a plurality of cell scrapers (e.g., a bank of cell scrapers (117)), as shown in FIG. 4B. In some embodiments, the incubator comprises two manipulators ($106_1$ and $106_2$), wherein each manipulator comprises a cell scraper (116), as shown in FIG. 4C. In some embodiments, the manipulator (106) is controlled by a controller (object (114) of FIG. 3) that is configured for programming of up to 360° rotation of the scraper tip/blade of the cell scraper (116), thus allowing for programming of scraping motion in coordination with linear motion in the x-, y-, and z-axis, e.g., such that a constant angle of attack is maintained between the scraper blade and the cells being scraped, regardless of culture vessel well geometry.

FIG. 5 depicts schematics of illustrative embodiments of cell scrapers. In some embodiments, a cell scraper comprises a proximal end (118) and a distal end (119), as shown in FIGS. 5A-5B. In some embodiments, the distal end of the cell scraper comprises a scraping blade (e.g., a scraping edge) (120), as shown in FIGS. 5A-5B. In some embodiments, a cell scraper comprises an opening (e.g., orifice) configured for transporting (e.g., aspirating cells and/or cell culture media) (121), as shown in FIG. 5B. In some embodiments, a cell scraper comprises an opening connected to a channel (122), as shown in FIG. 5B. In some embodiments, a channel is integrated into a cell scraper (e.g., running along the inside or outside of a cell scraper handle and/or scraping blade).

Figure 6A:
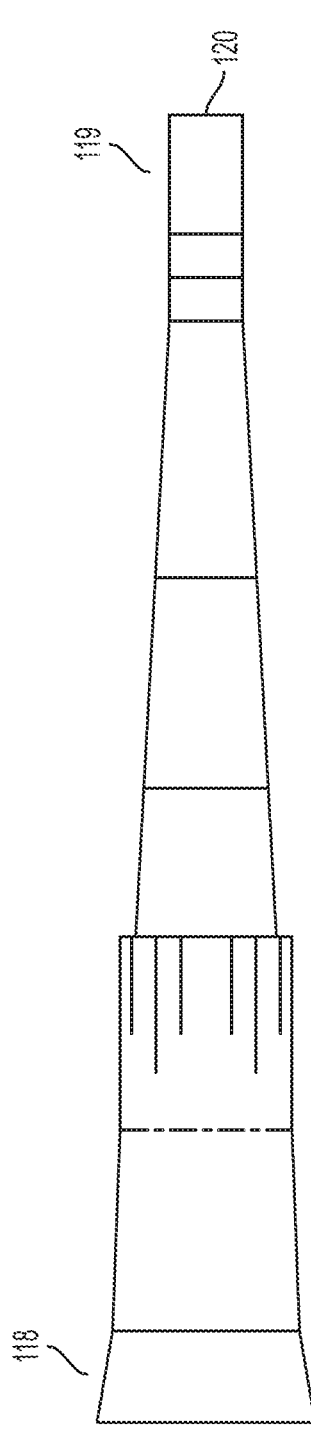
FIGS. 6A-6B are schematics of illustrative embodiments of cell scrapers.
Figure 6B:
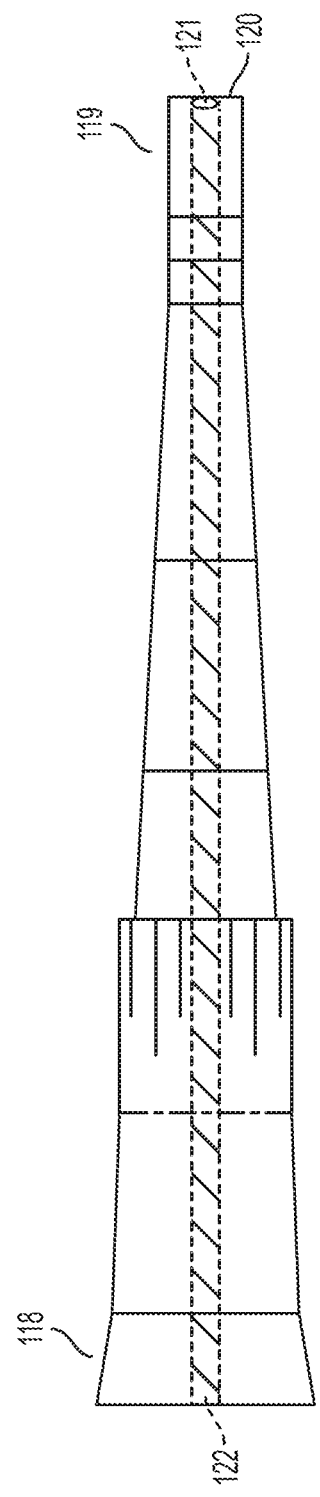

FIG. 6 depicts schematics of illustrative embodiments of cell scrapers. In some embodiments, a cell scraper comprises a proximal end (118) and a distal end (119), as shown in FIGS. 6A-6B. In some embodiments, the distal end of the cell scraper comprises a scraping blade (e.g., a scraping edge) (120), as shown in FIGS. 6A-6B. In some embodiments, a cell scraper comprises an opening (e.g., orifice) configured for transporting (e.g., aspirating, depositing, or aspirating and depositing) cells and/or cell culture media (121), as shown in FIG. 6B. In some embodiments, a scraper comprises an opening connected to a channel (122), as shown in FIG. 6B. In some embodiments, a channel is anchored to a wall of the cell scraper.

FIG. 7 depicts schematics of illustrative embodiments of cell scrapers. In some embodiments, a cell scraper comprises a proximal end (118) and a distal end (119), as shown in FIGS. 7A-7B. In some embodiments, the distal end of the cell scraper comprises a scraping blade (e.g., a scraping edge) (120), as shown in FIGS. 7A-7B. In some embodiments, the scraping edge is positioned at an angle relative to the scraper handle. In some embodiments, a cell scraper comprises an opening (e.g., orifice) configured for transporting (e.g., aspirating, depositing, or aspirating and depositing) cells and/or cell culture media (121), as shown in FIG. 7B. In some embodiments, a cell scraper further comprises an opening connected to a channel (122), as shown in FIG. 7B.

Figure 8B:
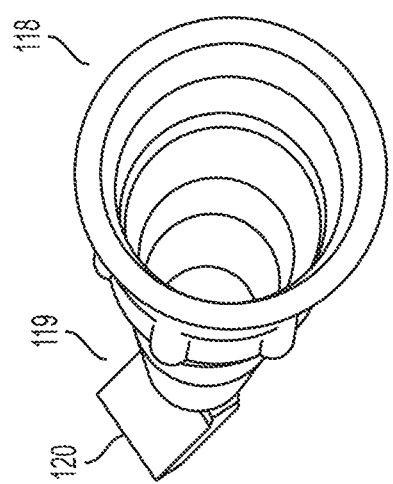
FIGS. 8A-8B are schematics of illustrative embodiments of cell scrapers.
Figure 8A:
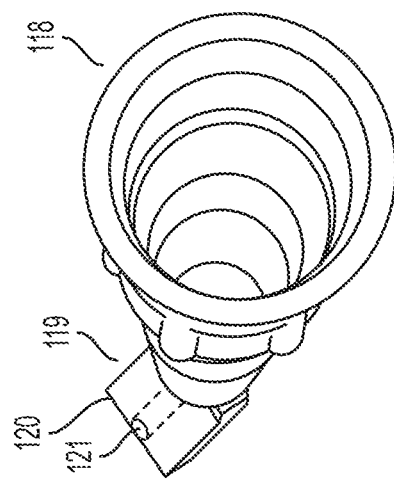

FIG. 8 depicts schematics of illustrative embodiments of cell scrapers. In some embodiments, a cell scraper comprises a proximal end (118) and a distal end (119), as shown in FIGS. 8A-8B. In some embodiments, the distal end of the cell scraper comprises a scraping blade (e.g., a scraping edge) (120), as shown in FIGS. 8A-8B. In some embodiments, the scraping edge is positioned at an angle relative to the scraper handle. In some embodiments, a cell scraper comprises an opening (e.g., orifice) configured for transporting (e.g., aspirating, depositing, or aspirating and depositing) cells and/or cell culture media (121), as shown in FIG. 8B. In some embodiments, a cell scraper comprises an opening connected to a channel (122), as shown in FIG. 8B. In some embodiments the channel walls are formed by the interior wall of the cell scraper, as shown in FIG. 8B.

Figure 9A:
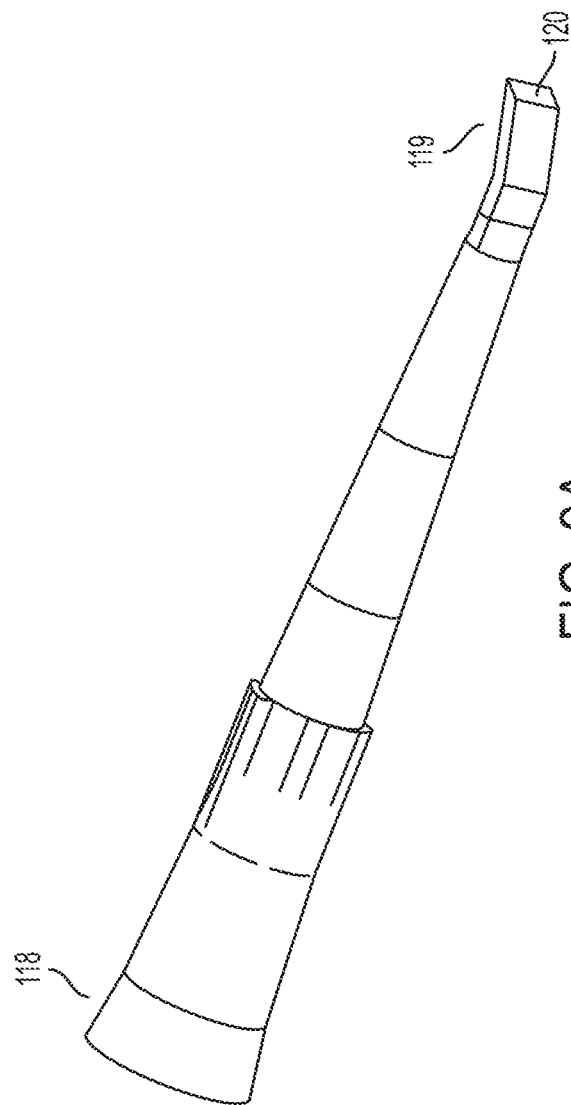
FIGS. 9A-9B are schematics of illustrative embodiments of cell scrapers.
Figure 9B:
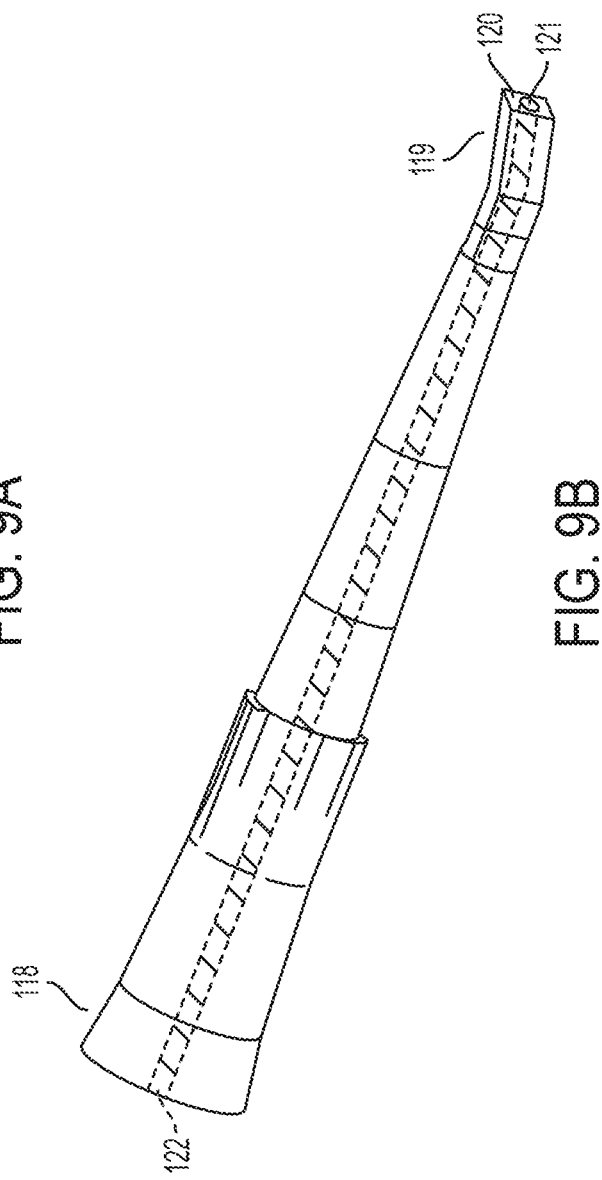

FIG. 9 depicts schematics of illustrative embodiments of cell scrapers. In some embodiments, a cell scraper comprises a proximal end (118) and a distal end (119), as shown in FIGS. 9A-9B. In some embodiments, the distal end of the cell scraper comprises a scraping blade (e.g., a scraping edge) (120), as shown in FIGS. 9A-9B. In some embodiments, the scraping edge is positioned at an angle relative to the scraper handle. In some embodiments, a cell scraper comprises an opening (e.g., orifice) configured for transporting (e.g., aspirating, depositing, or aspirating and depositing) cells and/or cell culture media (121), as shown in FIG. 9B. In some embodiments, an opening further comprises a channel (122), as shown in FIG. 9B. In some embodiments the channel walls are formed by the interior wall of the cell scraper, as shown in FIG. 9B.

FIG. 10 depicts schematics of illustrative embodiments of cell scrapers. In some embodiments, a cell scraper comprises a proximal end (118) and a distal end (119), as shown in FIGS. 10A-10B. In some embodiments, the distal end of the cell scraper comprises a scraping blade (e.g., a scraping edge) (120), as shown in FIGS. 10A-10B. In some embodiments, the scraping edge is positioned at an angle relative to the scraper handle. In some embodiments, a cell scraper comprises an opening (e.g., orifice) configured for transporting (e.g., aspirating, depositing, or aspirating and depositing) cells and/or cell culture media (121), as shown in FIG. 10B. In some embodiments, cell scraper comprises an opening connected to a channel (122), as shown in FIG. 10B. In some embodiments the channel walls are formed by the interior wall of the cell scraper, as shown in FIG. 10B.

Figure 11:
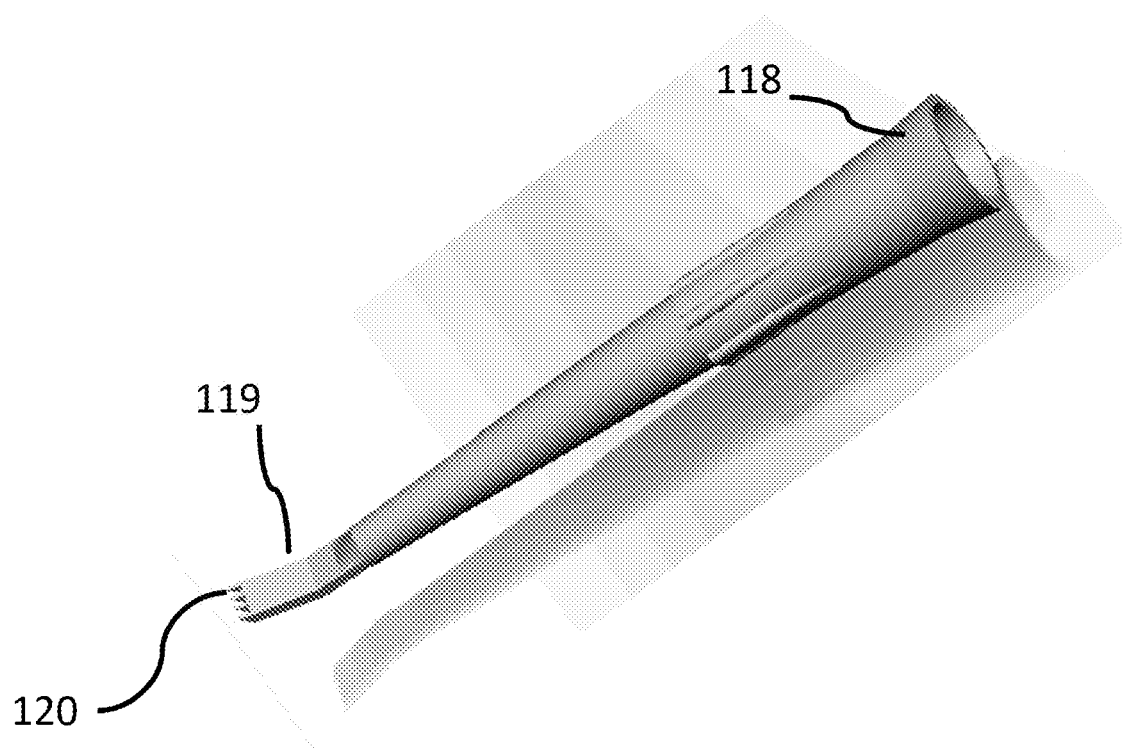
FIG. 11 shows a schematic of a cell scraper having a proximal end and a distal end comprising a scraper blade.

FIG. 11 depicts a schematic of illustrative embodiments of cell scrapers. In some embodiments, a cell scraper comprises a proximal end (118) and a distal end (119). In some embodiments, the distal end of the cell scraper comprises a scraping blade (e.g., a scraping edge) (120). In some embodiments, the scraping edge comprises multiple projections.

Figure 12:
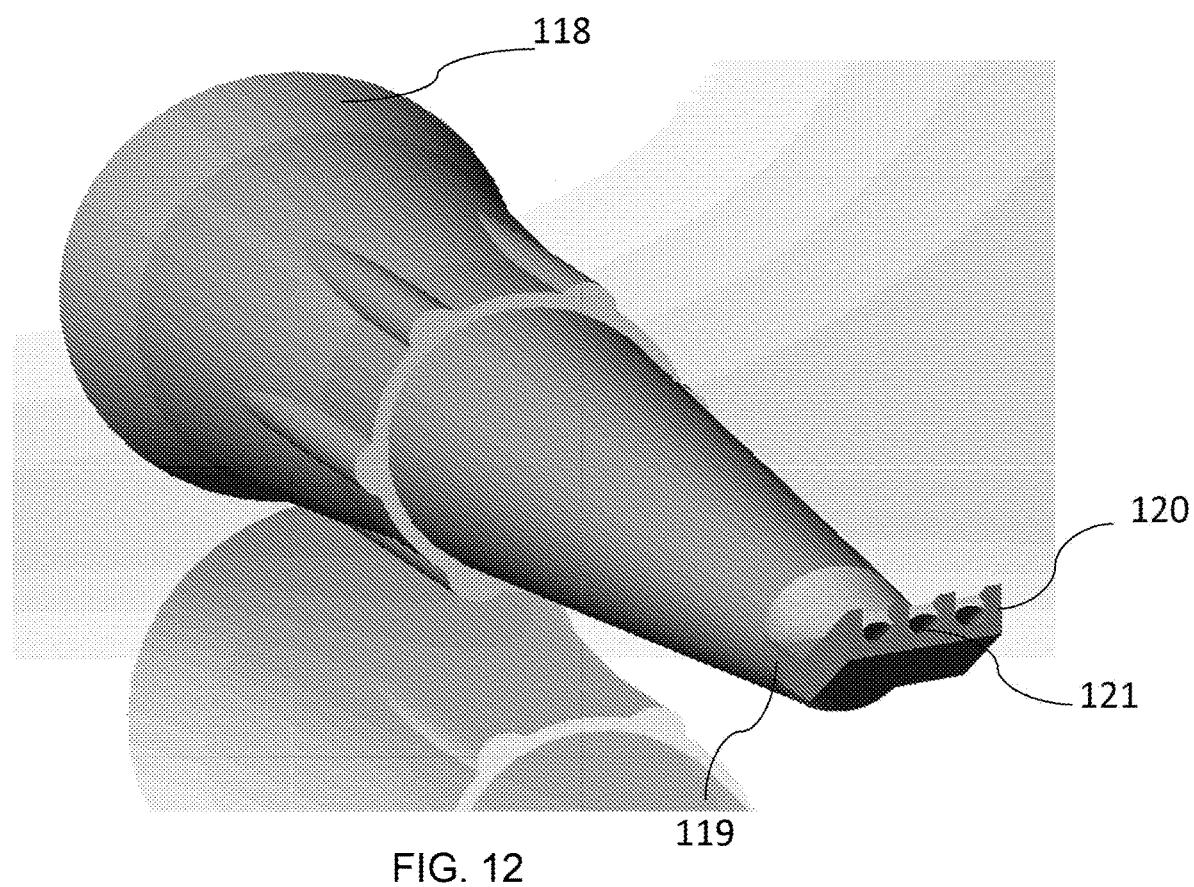
FIG. 12 shows a schematic of a cell scraper having a scraper blade comprising an opening and a channel (e.g., for aspirating cells and/or cell culture media).

FIG. 12 depicts a schematic of illustrative embodiments of cell scrapers. In some embodiments, a cell scraper comprises a proximal end (118) and a distal end (119). In some embodiments, the distal end of the cell scraper comprises a scraping blade (e.g., a scraping edge) (120). In some embodiments, the scraping edge comprises multiple projections. In some embodiments, a cell scraper comprises an opening (e.g., orifice) configured for transporting (e.g., aspirating, depositing, or aspirating and depositing) cells and/or cell culture media (121). In some embodiments, cell scraper comprises an opening connected to a channel (not shown). In some embodiments the channel walls are formed by the interior wall of the cell scraper.

Figure 13:
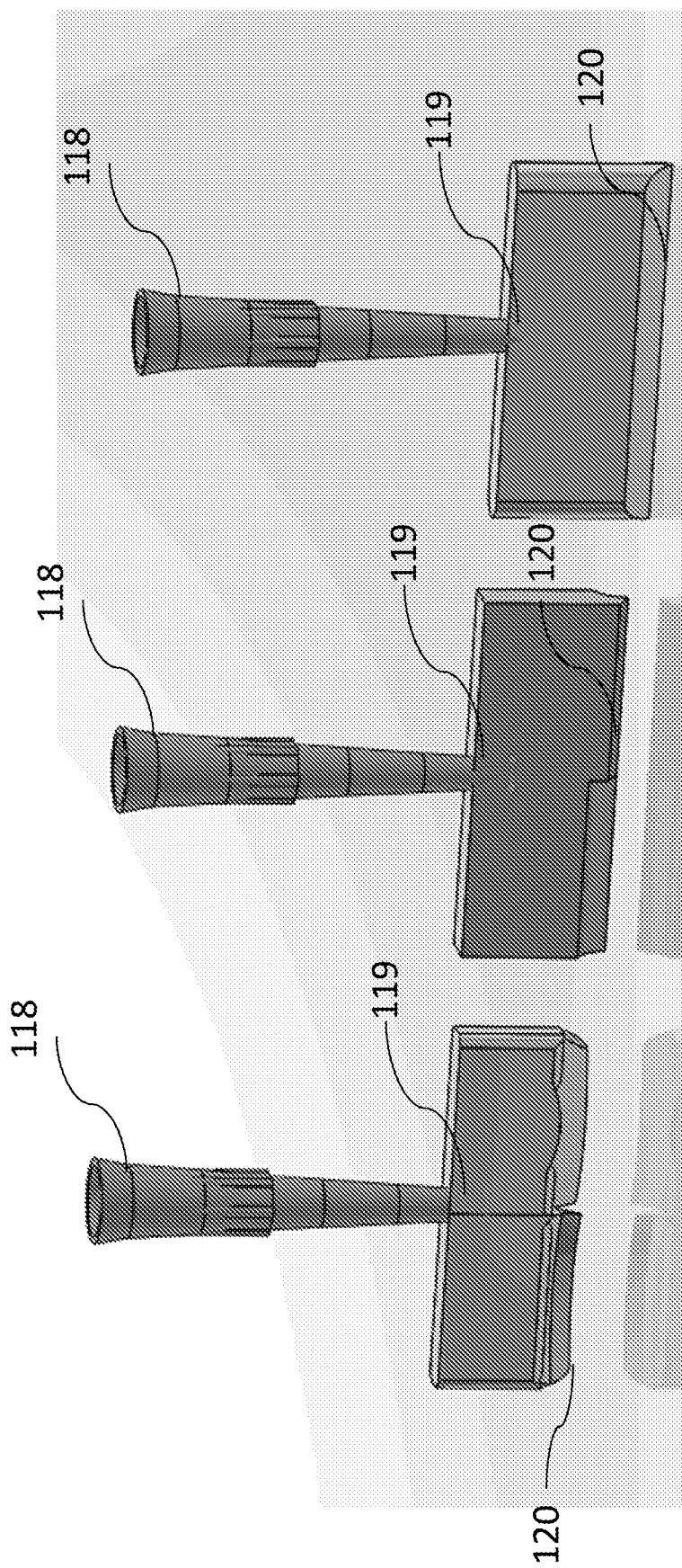
FIGS. 13A-13C are schematics of illustrative embodiments of cell scrapers having a proximal end and a distal end comprising a scraper blade.

FIG. 13 depicts schematics of illustrative embodiments of cell scrapers. In some embodiments, a cell scraper comprises a proximal end (118) and a distal end (119), as shown in FIGS. 13A-13C. In some embodiments, the distal end of the cell scraper comprises a scraping blade (e.g., a scraping edge) (120), as shown in FIGS. 13A-13C. In some embodiments, the scraping edge is positioned at an angle relative to the scraper handle.

Figure 14:
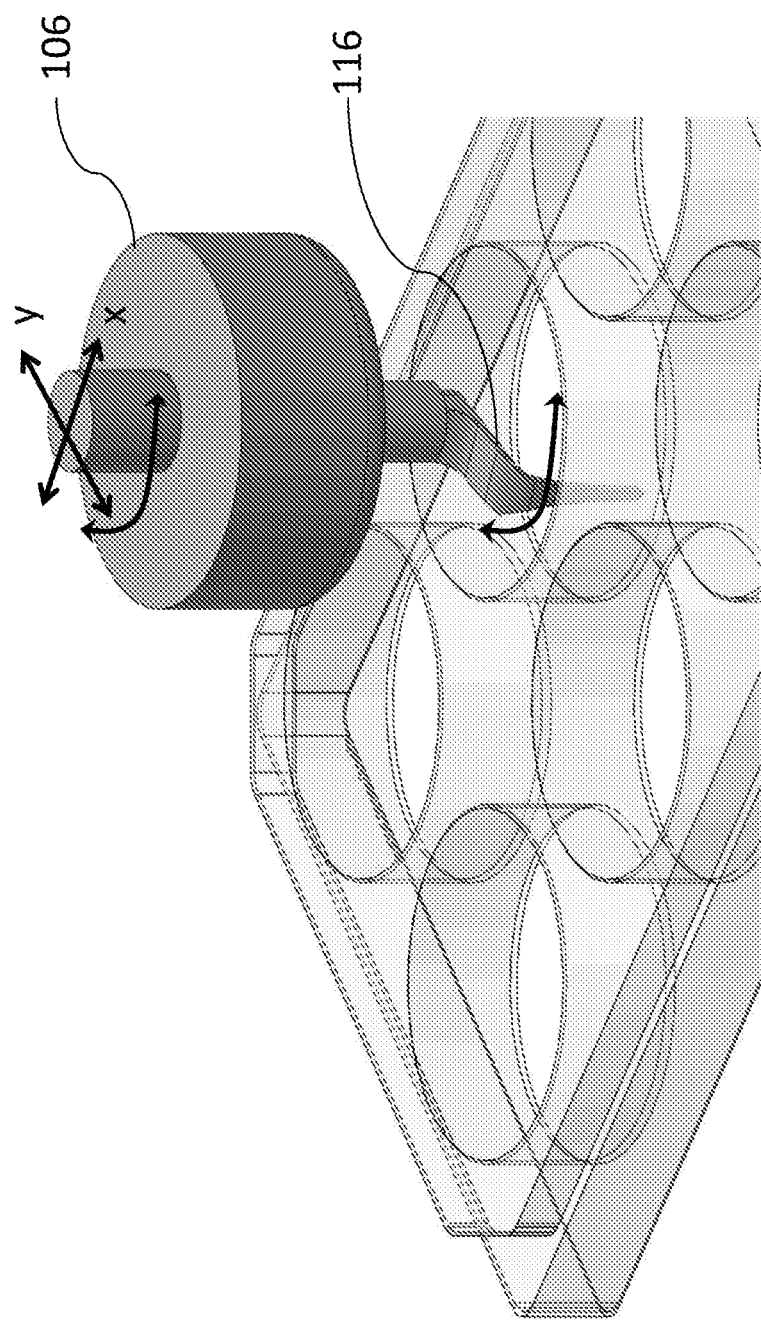
FIG. 14 is a schematic of a manipulator comprising a cell scraper with a depiction of the range of motion along x-, y- and z-axes of a manipulator comprising a cell scraper.

FIG. 14 depicts a schematic of a manipulator (106) comprising a cell scraper (116). In some embodiments, the manipulator (106) is controlled by a controller (not shown) that is configured for programming of up to 360° rotational oscillation or linear oscillation of the scraper tip/blade of the cell scraper (116), thus allowing for programming of scraping motion in coordination with linear motion in the x-, y-axis and rotational motion around the z-axis, e.g., such that a constant angle of attack is maintained between the scraper blade and the cells being scraped, regardless of culture vessel well geometry.

Figure 15A:
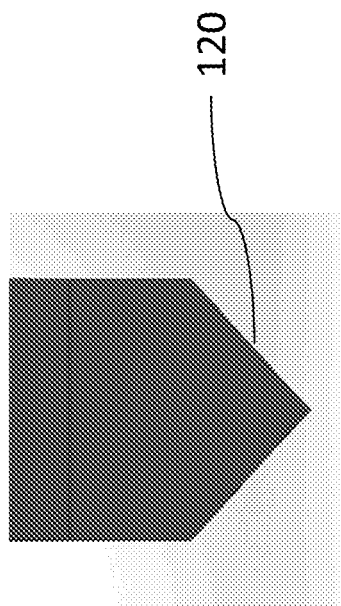
FIGS. 15A-15C are schematics of illustrative embodiments of cell scrapers.
Figure 15B:
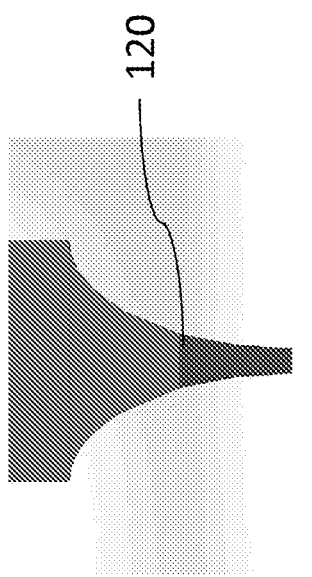
Figure 15C:
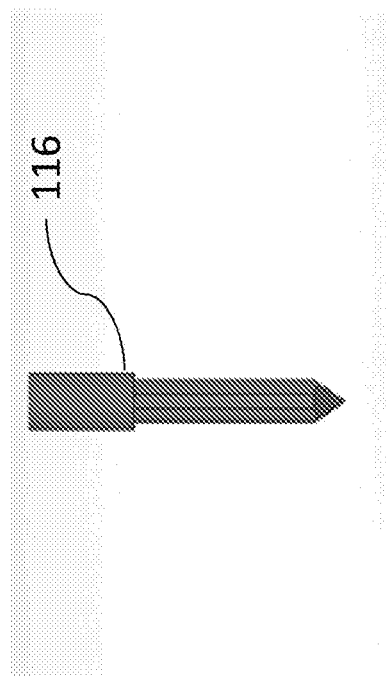

FIG. 15 depicts schematics of illustrative embodiments of cell scrapers (116). In some embodiments, the distal end of the cell scraper comprises a scraping blade (e.g., a scraping edge) (120), as shown in FIGS. 15B-15C.

Automated Cell Culture

This document relates to incubators and methods for culturing, manipulating, and/or monitoring cells under controlled conditions (e.g., under aseptic and/or sterile conditions). In some aspects, incubators and methods include automated components. In some aspects, incubators and methods are useful for long term cell culture (e.g., to grow and maintain cells for recombinant protein expression or to grow and/or differentiate cells for therapeutic applications such as implantation). In some embodiments, cell cultures are grown within a culture vessel in an incubator described herein.

Culture Vessel

Cell culture vessels may be configured for culturing cells of different types, including eukaryotic or prokaryotic cells. In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis*, or *Pischia pastoris* cells, or bacterial cells such as *Escherichia coli, Bacillus subtilis*, or *Corynebacterium* cells), insect cells (e.g., *Drosophila* cells, or Sf9 or Sf21 cells), plant cells (e.g., algal cells) or cells of any other type.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example, HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells) and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, *Xenopus* cell lines, plant cell lines, or any other cell. In some embodiments, cells are human 293 cells (e.g., 293-T or HEK 293 cells), murine 3T3 cells, Chinese hamster ovary (CHO) cells, CML T1 cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to, solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators described herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

Primary Cell Isolation

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or proteinase are used to digest the extracellular matrix. In some embodiments, tissue or biological samples are placed in culture medium (e.g., with or without physical or enzymatic disruption), and cells that are released and that grow in the culture medium can be isolated for further culture.

Cell Culture

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated within the incubators.

In some aspects, devices and methods described herein provide and maintain appropriate temperature and gas mixtures for cell growth. It should be appreciated that cell growth conditions differ for different cell types and that devices described herein can be programmed to maintain different conditions. In some embodiments, conditions of approximately 37° C., and 5% $CO_2$ are used for mammalian cells.

In some embodiments, devices and methods described herein are used to monitor or assay the culture media for nutrient depletion, changes in pH, changes in temperature, accumulation of apoptotic or necrotic cells, and/or cell density. For example a manipulator (106) may include sensors that monitor culture media. In some embodiments, devices and methods described herein are used to modify or change the culture media or conditions and/or to passage the cells when appropriate. In some embodiments, the devices and methods are automated (e.g., controlled by a controller (114) and/or computer (111), as shown in FIG. 3).

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture in incubators and vessels described herein. For example, cell cultures may be transfected with nucleic acids (e.g., DNA or RNA) or exposed to viral infection (e.g., using recombinant virus particles to deliver DNA or RNA).

Aseptic techniques can be used to prevent or minimize contamination of cell cultures during growth and manipulation. In some embodiments equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example in an environment (e.g., within an incubator chamber) that has been disinfected and in which the air has been filtered to remove potential contaminants.

In some embodiments, cell cultures are grown and maintained under GMP-compliant conditions, including using GMP-compliant media or GMP-compliant liquid handling equipment and performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by *Mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells being grown in culture (e.g., mammalian cells). In some embodiments, one or more molecular detection assays (e.g., PCR, ELISA, RNA labeling, or other enzymatic techniques) or cell-based assays can be used to detect contamination (e.g., *Mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat-STR-fingerprinting), isoenzyme analysis, human lymphocyte antigen (HLA) typing, chromosomal analysis, karyotyping, cell morphology, or other techniques.

In some embodiments, cells produced using devices and methods provided herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be present in or in proximity with an incubator to facilitate freezing of cells isolated from cell cultures.

Cell Culture Incubators:

This document relates to incubators and methods for culturing, manipulating, and/or monitoring cells under controlled conditions (e.g., under aseptic and/or sterile conditions). In some embodiments, the cell culture incubators provided herein include an incubator cabinet defining an internal chamber for incubation of cells in one or more cell culture vessels, in which the internal chamber is configured to hold the one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example to provide alternative access to the internal chamber during periods of time when the incubator is not operational, e.g., during maintenance of the incubator. In some embodiments, the incubators include a storage location within the internal chamber for storing one or more cell culture vessels. In some embodiments, a cell culture vessel transfer device is provided in the incubator for moving one or more cell culture vessels from a first imaging location to a storage location and/or from a storage location to an first imaging location.

In some embodiments, incubators or incubator cabinets provided herein are rectangularly cuboidal in shape. In some embodiments incubators or incubator cabinets provided herein have a rectangular footprint in a range of 1 $ft^2$ to 16 $ft^2$. In some embodiments incubators or incubator cabinets provided herein have a rectangular footprint of up to about 1 $ft^2$, 2 $ft^2$, 3 $ft^2$, 4 $ft^2$, 5 $ft^2$, 6 $ft^2$, 7 $ft^2$, 8 $ft^2$, 9 $ft^2$, 10 $ft^2$, $ft^2$, 12 $ft^2$, 13 $ft^2$, $ft^2$, 15 $ft^2$, or 16 $ft^2$. In some embodiments incubators or incubator cabinets provided herein have a total chamber volume in a range of 1 $ft^3$ to 100 $ft^3$. In some embodiments incubators or incubator cabinets provided herein have a chamber volume of up to about 1 $ft^3$, 5 $ft^3$, 10 $ft^3$, 25 $ft^3$, 50 $ft^3$ or 100 $ft^3$. In some embodiments incubators or incubator cabinets provided herein have a rectangular footprint in a range of 0.09 m² to 1.78 m². In some embodiments incubators or incubator cabinets provided herein have a rectangular footprint of up to about 0.1 m², 0.2 m², 0.3 m², 0.4 m², 0.5 m², 0.6 m², 0.7 m², 0.8 m², 0.9 m², 1.0 m², 1.1 m², 1.2 m², 1.3 m², 1.4 m², 1.5 m², 1.6 m², or 1.7 m². In some embodiments, incubators or incubator cabinets provided herein have a total chamber volume in a range of 0.03 m³ to 3 m³. In some embodiments incubators or incubator cabinets provided herein have a chamber volume of up to about 0.03 m³, 0.1 m³, 0.3 m³, 1 m³, or 3 m³.

Materials

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

Monitoring Equipment

In some embodiments, the environment inside an incubator is controlled by a control system that may be configured to control the temperature, humidity, carbon dioxide, oxygen, and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber having a storage location. In some embodiments, the incubator is further provided with a monitoring system with predefined sensors. Examples of monitoring devices include, but are not limited, to oxygen monitors, carbon dioxide monitors, ozone gas detectors, hydrogen peroxide monitors and multi gas monitors. For example, in some embodiments, an incubator advantageously includes a plurality of sensors responsive to different parameters relevant to cell growth, which may include temperature, air purity, contaminant levels, pH, humidity, $N_2$, $CO_2$, $O_2$, and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed herein.

In some embodiments, an environmental monitoring system can be used in conjunction with an incubator described herein. In some embodiments, one or more sensors that provide for the measurement of temperature, air composition (e.g., $CO_2$ concentration, $O_2$ concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include $CO_2$ sensors, $O_2$ sensors, $N_2$ sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of $CO_2$ in an incubator may be increased upon indication from a $CO_2$ sensor that a lower than desirable concentration of $CO_2$ is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents.

In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator). In some embodiments, one or more controllers are attached to the sensors and other systems to control the internal environment of the incubator.

In some embodiments, an incubator can include one or more light sources (e.g., an incandescent bulb, LED, UV or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

Seals

In some embodiments, a culture cabinet includes windows, doors, or openings that when closed are sealed to preserve sterility after the incubator cabinet has been sterilized. In some embodiments, each seal of the incubator cabinet is air tight up to a threshold level of pressure (e.g., up to 1 atm). In some embodiments, a gasket is provide to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoro-ethylene). It is often desirable that a gasket be made from a material that provides some degree of yielding such that it is able to deform and tightly fills the space it is designed for, including any slight irregularities. In some embodiments, gaskets can be used with an application of sealant directly to the gasket surface to function properly. In some embodiments, a gasket material can include a closed-cell neoprene foam which is non-reactive with carbon dioxide or ozone.

Transfer Devices

Incubators disclosed herein typically include one or more transfer devices for moving one or more items, e.g., from a first location to a second location, within the incubators. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In some embodiments, a transfer device includes a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further includes a gripper assembly coupled to a robotic arm. In some embodiments, the gripper assembly includes one or more grippers mounted on the end of the robotic arm, each gripper having two or more (e.g., 3, 4, 5, or more) gripper fingers. In some embodiments, each of the gripper fingers on the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, or the platform, or a separate absolute encoder for each of the gripper assembly and/or the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt, located, for example, on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components from a transport line of the laboratory automation system into the incubator cabinet or transport external assay components into and/or out of the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are is located. In some cases, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to position properly the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner.

In some embodiments, a sensor or other feature is provided to detect when one or more doors of an incubator is opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station.

The information can be used to control operation of a transfer device, e.g., a robotic arm, within the incubator cabinet to ensure that the transfer device can grab, manipulate, or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel, and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself can be configured to determine the height or other dimensions of the vessel or other container. Using this information, the robotic arm may be requested to transport a particular container, such as when an analytical module is ready to perform an assay or other manipulation on cells grown in the vessels or has completed performing an assay or manipulation.

Computer and Control Equipment

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Cell Assays

In some embodiments, incubator cabinets provided herein are configured with a microscope or other imager or other device for purposes of monitoring cell growth, viability or other aspect of cells. In some embodiments, the microscope or imager is used in conjunction with an assay performed within the incubator cabinet, such as an image based phenotypic screen or assay.

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

Treatments and Experimental Interventions

In certain embodiments, incubators provided herein are configured to permit high-throughput screening (HTS) within an incubator cabinet. In some embodiments, HTS refers to testing of up to, for example, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays described herein involve the use of automation. In some embodiments, an integrated robot system that includes of one or more robotic arms transports assay microplates between multiple assay stations for compound, cell, and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

The above aspects and embodiments may be employed in any suitable combination, as the present invention is not limited in this respect.

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g., "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cell culture incubator comprising:
   an incubator cabinet comprising an internal chamber for incubation of cells in one or more cell culture vessels;
   a door opening from an external environment to the internal chamber;
   at least two imagers configured for imaging the cells within the internal chamber;
   a manipulator for manipulating the cells in the one or more cell culture vessels within the internal chamber;
   a cell culture vessel transfer device for moving the one or more cell culture vessels between the at least two imagers within the internal chamber; and
   a controller configured for controlling the cell culture transfer device to move cell culture vessels between the at least two imagers.

2. The incubator of claim 1, wherein the at least two imagers comprise phase contrast microscopes.

3. The incubator of claim 1, wherein the at least two imagers comprise bright-field microscopes.

4. The incubator of claim 1, wherein the at least two imagers produce phase shift images.

5. The incubator of claim 4, further comprising an image processor for segmenting and analyzing the phase shift images.

6. The incubator of claim 1, wherein the at least two imagers image the cell culture vessels from a variety of angles.

7. The incubator of claim 1, wherein the at least two imagers produce phase shift images and wherein the phase shift images are image processed to provide an unstained cell count.

8. A cell culture incubator comprising:
an incubator cabinet comprising an internal chamber for incubation of cells in one or more cell culture vessels;
a door opening from an external environment to the internal chamber;
at least one imager configured for imaging the cells within the internal chamber, wherein the at least one imager images the cell culture vessels from a variety of angles;
a manipulator for manipulating the cells in the one or more cell culture vessels within the internal chamber;
a cell culture vessel transfer device for moving the one or more cell culture vessels between the at least one imager and the manipulator within the internal chamber; and
a controller configured for controlling the cell culture transfer device to move cell culture vessels.

9. The incubator of claim 8, wherein the at least one imager comprises a phase contrast microscope.

10. The incubator of claim 8, wherein the at least one imager comprises bright-field microscope.

11. The incubator of claim 10, wherein the at least one imager produces phase shift images.

12. The incubator of claim 11, further comprising an image processor for segmenting and analyzing the phase shift images.

13. The incubator of claim 8, wherein the at least one imager produces phase shift images and wherein the phase shift images are image processed to provide an unstained cell count.

* * * * *